US012559289B2

(12) United States Patent
Jüngst et al.

(10) Patent No.: US 12,559,289 B2
(45) Date of Patent: Feb. 24, 2026

(54) AROMA CONTAINER

(71) Applicant: air up group GmbH, Munich (DE)

(72) Inventors: Magdalena Jüngst, Munich (DE); Jannis Koppitz, Munich (DE); Tim Jäger, Munich (DE); Fabian Schlang, Munich (DE)

(73) Assignee: air up group GmbH, Munich (DE)

( * ) Notice: Subject to any disclaimer, the term of this patent is extended or adjusted under 35 U.S.C. 154(b) by 193 days.

(21) Appl. No.: 17/925,742

(22) PCT Filed: May 18, 2020

(86) PCT No.: PCT/EP2020/063793
§ 371 (c)(1),
(2) Date: Mar. 22, 2023

(87) PCT Pub. No.: WO2021/233516
PCT Pub. Date: Nov. 25, 2021

(65) Prior Publication Data
US 2023/0312197 A1 Oct. 5, 2023

(51) Int. Cl.
B65D 51/28 (2006.01)
A47G 19/22 (2006.01)
(Continued)

(52) U.S. Cl.
CPC ..... B65D 51/2892 (2013.01); A47G 19/2205 (2013.01); A61L 9/12 (2013.01);
(Continued)

(58) Field of Classification Search
CPC ..... A23L 27/70; A23L 27/88; A47G 19/2205; A47G 2400/04; A47G 21/183; A61L 9/12;
(Continued)

(56) References Cited

U.S. PATENT DOCUMENTS

| | | | | |
|---|---|---|---|---|
| 2,642,310 A | * | 6/1953 | Meek | A61L 9/12 239/35 |
| 2,738,225 A | * | 3/1956 | Meek | A61L 9/12 96/147 |

(Continued)

FOREIGN PATENT DOCUMENTS

| | | |
|---|---|---|
| CA | 3 240 653 A1 | 6/2023 |
| CN | 2389124 Y | 7/2000 |

(Continued)

OTHER PUBLICATIONS

International Search Report and Written Opinion dated Sep. 28, 2021, in connection with International Application No. PCT/EP2021/070240.

(Continued)

*Primary Examiner* — Gideon R Weinerth
(74) *Attorney, Agent, or Firm* — Fish & Richardson P.C.

(57) ABSTRACT

An aroma container for adding an aroma substance to an air flow flowing through the aroma container. The aroma container comprises an upper wall, a lower wall and at least one side wall, which surround an aroma chamber. The container includes at least one air inlet opening into the aroma chamber, and at least one air outlet opening out of the aroma chamber, wherein a carrier substance for the aroma substance is present in the aroma chamber. A head space may be provided between the carrier substance and the side of the upper wall facing the aroma chamber. The carrier substance comprises a nonwoven material, wherein the air permeability L of the nonwoven material at a differential pressure of 100 Pa is L≥200 l/(m²·s), and preferably between 220 l/(m²·s) and 280 l/(m²·s).

33 Claims, 16 Drawing Sheets

(51) Int. Cl.
    *A61L 9/12*        (2006.01)
    *B65D 43/02*     (2006.01)
(52) U.S. Cl.
    CPC ...... B65D 43/0231 (2013.01); *A47G 2400/04*
        (2013.01); *A61L 2209/133* (2013.01); *B65D*
        *2203/12* (2013.01); *B65D 2543/00092*
        (2013.01); *B65D 2543/00537* (2013.01)
(58) Field of Classification Search
    CPC ............... A61L 9/127; A61L 2209/133; A61L
        2209/13; B65D 43/0231; B65D 51/2892;
        B65D 2543/00092; B65D 2543/00537;
        B65D 2203/12; B65D 51/28; B65D
        2517/5091; A61M 2021/0016; A61M
        2210/0618; A61J 17/101
    USPC .......................................... 220/212; 239/57
    See application file for complete search history.

(56)             References Cited

U.S. PATENT DOCUMENTS

| | | | | |
|---|---|---|---|---|
| 3,043,464 | A * | 7/1962 | Cerasari | ................. A61J 11/045 |
| | | | | 215/11.1 |
| 3,717,476 | A | 2/1973 | Harvey | |
| 4,014,501 | A * | 3/1977 | Buckenmayer | ........ B65D 85/00 |
| | | | | 220/361 |
| 4,493,460 | A | 1/1985 | Buss | |
| 4,549,693 | A * | 10/1985 | Barlics | ...................... A61L 9/12 |
| | | | | 206/0.5 |
| 4,955,503 | A | 9/1990 | Propes | |
| 5,165,603 | A | 11/1992 | Hahn | |
| 5,230,867 | A * | 7/1993 | Kunze | ...................... A61L 9/12 |
| | | | | 239/57 |
| 5,635,229 | A | 6/1997 | Ray | |
| 5,810,003 | A * | 9/1998 | Findlater | ............... A61M 15/00 |
| | | | | 215/11.1 |
| 6,045,833 | A * | 4/2000 | Landau | .................. B65D 51/00 |
| | | | | 426/106 |
| 6,050,551 | A * | 4/2000 | Anderson | ............... A61L 9/122 |
| | | | | 261/DIG. 65 |
| 6,076,450 | A | 6/2000 | DiGiorgio, Jr. | |
| 6,112,749 | A | 9/2000 | Hall et al. | |
| 6,314,866 | B1 | 11/2001 | Melton | |
| 6,502,712 | B1 | 1/2003 | Weber-Unger | |
| 6,578,726 | B1 | 6/2003 | Schaefer | |
| 6,857,579 | B2 * | 2/2005 | Harris | ................. A01M 1/2077 |
| | | | | 239/57 |
| 7,005,152 | B2 | 2/2006 | Landau | |
| 7,528,102 | B2 * | 5/2009 | Barthel | ................. D06F 58/203 |
| | | | | 512/1 |
| 7,631,814 | B2 * | 12/2009 | Zarembinski | ............. A61L 9/12 |
| | | | | 239/58 |
| 8,020,785 | B2 * | 9/2011 | Chao | ...................... A61Q 15/00 |
| | | | | 239/58 |
| 8,272,532 | B2 | 9/2012 | Michaelian et al. | |
| 8,662,294 | B2 | 3/2014 | Benbassat | |
| 8,662,339 | B2 | 3/2014 | Sprunger | |
| 9,010,238 | B2 | 4/2015 | Bodum | |
| 9,603,471 | B2 * | 3/2017 | Green | ................. A47G 19/2272 |
| 9,795,242 | B2 | 10/2017 | Waggoner et al. | |
| 9,801,969 | B2 * | 10/2017 | Griffis | ................. B65D 1/0246 |
| 9,968,209 | B2 | 5/2018 | Maranon | |
| 10,328,172 | B2 | 6/2019 | Griffis | |
| 10,744,223 | B2 * | 8/2020 | Griffis | .................... B65D 23/12 |
| 11,097,877 | B2 * | 8/2021 | Griffis | ................. B65D 47/243 |
| D939,955 | S * | 1/2022 | Jüngst | ........................... D9/435 |
| 11,312,528 | B2 * | 4/2022 | Griffis | .................... B65D 5/40 |
| 11,564,516 | B2 | 1/2023 | Jäger et al. | |
| 11,793,336 | B2 | 10/2023 | Jäger et al. | |
| 11,986,576 | B2 * | 5/2024 | Bing | ........................ A61L 9/012 |
| 12,232,639 | B2 | 2/2025 | Jungst | |
| 2001/0042546 | A1 | 11/2001 | Umeda et al. | |
| 2002/0036239 | A1 | 3/2002 | Banach | |

| | | | | |
|---|---|---|---|---|
| 2002/0190023 | A1 * | 12/2002 | Landau | .............. A47G 19/2227 |
| | | | | 215/387 |
| 2004/0028779 | A1 * | 2/2004 | Landau | .............. A47G 19/2227 |
| | | | | 426/132 |
| 2004/0261807 | A1 | 12/2004 | Dube et al. | |
| 2005/0224595 | A1 * | 10/2005 | Kuiper | .................... A61L 9/122 |
| | | | | 239/57 |
| 2005/0274819 | A1 * | 12/2005 | Reed | ......................... A61L 9/12 |
| | | | | 239/57 |
| 2006/0283888 | A1 * | 12/2006 | Kinscherf | ........... B65D 1/0223 |
| | | | | 222/192 |
| 2007/0001023 | A1 * | 1/2007 | Green | ..................... A61L 9/042 |
| | | | | 239/34 |
| 2007/0062961 | A1 | 3/2007 | Rigas | |
| 2007/0088314 | A1 | 4/2007 | Gollier | |
| 2007/0228184 | A1 * | 10/2007 | Chen | ...................... A45D 34/02 |
| | | | | 239/58 |
| 2008/0000898 | A1 | 1/2008 | Ramsden | |
| 2008/0028353 | A1 | 1/2008 | Lu et al. | |
| 2008/0128427 | A1 | 6/2008 | Friedman | |
| 2008/0230079 | A1 | 9/2008 | Besso et al. | |
| 2008/0257853 | A1 | 10/2008 | Cappello | |
| 2009/0159595 | A1 | 6/2009 | Michaelian et al. | |
| 2009/0250479 | A1 | 10/2009 | Kaufman et al. | |
| 2009/0266829 | A1 | 10/2009 | Bailey | |
| 2011/0094904 | A1 | 4/2011 | Lee | |
| 2011/0155732 | A1 | 6/2011 | Sprunger | |
| 2012/0261375 | A1 | 10/2012 | Loging | |
| 2013/0043245 | A1 * | 2/2013 | Griffis | .................... B65D 41/34 |
| | | | | 239/34 |
| 2013/0302477 | A1 | 11/2013 | Salinas | |
| 2013/0330438 | A1 * | 12/2013 | Osterbauer | ........... A61J 17/101 |
| | | | | 215/11.1 |
| 2014/0166680 | A1 | 6/2014 | St. Gelais | |
| 2015/0030726 | A1 | 1/2015 | Binder et al. | |
| 2016/0046407 | A1 | 2/2016 | Lee | |
| 2017/0239382 | A1 | 8/2017 | Griffis | |
| 2018/0000269 | A1 | 1/2018 | San Miguel et al. | |
| 2018/0127159 | A1 * | 5/2018 | Cunningham | ..... B65D 51/2807 |
| 2018/0147484 | A1 | 5/2018 | Osawa et al. | |
| 2018/0353636 | A1 * | 12/2018 | Hafer | .................... B05B 7/0081 |
| 2019/0367230 | A1 | 12/2019 | Griffis | |
| 2020/0054778 | A1 | 2/2020 | Burns et al. | |
| 2020/0178712 | A1 | 6/2020 | Jäger et al. | |
| 2022/0087456 | A1 | 3/2022 | Jäger et al. | |
| 2023/0009630 | A1 * | 1/2023 | Chandler | ............... A61K 47/10 |
| 2023/0270270 | A1 | 8/2023 | Jungst et al. | |
| 2023/0312197 | A1 * | 10/2023 | Jüngst et al. | ............. A61L 9/12 |
| | | | | 220/212 |
| 2023/0372646 | A1 * | 11/2023 | Tsang | .................... A61M 15/08 |
| 2023/0405321 | A1 * | 12/2023 | Ranasinghe | ......... A61N 1/0546 |
| 2024/0000249 | A1 | 1/2024 | Jäger et al. | |
| 2024/0066173 | A1 * | 2/2024 | Luque Vera | .............. A61L 9/12 |
| 2024/0067416 | A1 * | 2/2024 | Li | .......................... B65D 51/28 |
| 2024/0124204 | A1 * | 4/2024 | Palzer | .................... B65D 65/40 |
| 2024/0148172 | A1 * | 5/2024 | Schlang | ............ A47G 19/2227 |
| 2025/0009155 | A1 | 1/2025 | Jager et al. | |
| 2025/0151936 | A1 | 5/2025 | Biczo et al. | |
| 2025/0169633 | A1 | 5/2025 | Jungst et al. | |
| 2025/0289634 | A1 * | 9/2025 | Schlang | ............ A47G 19/2227 |

FOREIGN PATENT DOCUMENTS

| | | |
|---|---|---|
| CN | 2461872 Y | 11/2001 |
| CN | 101578053 A | 11/2009 |
| CN | 106820859 A | 6/2017 |
| CN | 206380892 U1 | 8/2017 |
| DE | 20 2016 004 961 U1 | 9/2016 |
| DE | 20 2017 000 239 U1 | 1/2017 |
| DE | 20 2018 000 382 U1 | 5/2018 |
| DE | 10 2018 003 669 A1 | 1/2019 |
| DE | 10 2018 222 299 A1 | 6/2020 |
| DE | 20 2021 101 790 U1 | 7/2022 |
| DE | 20 2023 102 688 U1 | 6/2023 |
| EP | 1 056 660 A1 | 3/2005 |
| EP | 2 215 936 A1 | 8/2010 |
| EP | 2496118 B1 | 10/2013 |
| EP | 3 944 792 A1 | 2/2022 |

(56)                  References Cited

FOREIGN PATENT DOCUMENTS

| | | | |
|---|---|---|---|
| EP | 4 321 061 | A1 | 2/2024 |
| GB | 2 401 527 | A | 11/2004 |
| JP | S52-070583 | U | 11/1950 |
| JP | S56-101090 | U | 12/1954 |
| JP | H02-100480 | U | 8/1990 |
| JP | H02-274252 | A | 11/1990 |
| JP | 2000-085777 | A | 3/2000 |
| JP | 2001-299916 | A | 10/2001 |
| JP | 2002-037304 | A | 2/2002 |
| JP | 2004-026304 | A | 1/2004 |
| JP | 2006-520722 | A | 9/2006 |
| JP | H03-129314 | U | 2/2007 |
| JP | 2008-104557 | A | 5/2008 |
| JP | 2008-150056 | A | 7/2008 |
| JP | 2011-507771 | A | 3/2011 |
| JP | 2012-020783 | A | 2/2012 |
| JP | 2013-121556 | A | 6/2013 |
| JP | 2015-051781 | A | 3/2015 |
| JP | 2017-030791 | A | 2/2017 |
| JP | 2018-188221 | A | 11/2018 |
| KR | 20-2016-0004174 | U1 | 12/2016 |
| RU | 1326971 | U1 | 9/2013 |
| WO | WO 2003/013977 | A1 | 2/2003 |
| WO | WO 2016/199441 | A1 | 12/2016 |
| WO | WO 2019/016096 | A1 | 1/2019 |
| WO | WO 2019/101973 | A1 | 5/2019 |
| WO | WO 2020/054988 | A1 | 3/2020 |
| WO | WO 2020/126210 | A1 | 6/2020 |
| WO | WO 2021/233516 | A1 | 11/2021 |
| WO | WO 2022/111808 | A1 | 6/2022 |
| WO | WO 2022/184823 | A1 | 9/2022 |

OTHER PUBLICATIONS

International Search Report and Written Opinion dated May 2, 2023, in connection with International Application No. PCT/EP2023/053361, with English translation thereof.

International Search Report and Written Opinion mailed Oct. 23, 2023 for International Application No. PCT/EP2023/071697.

International Search Report and Written Opinion mailed Feb. 19, 2021, in connection with International Application No. PCT/EP2020/063793, with English translation thereof.

Galileo, "Wie reines Leitungswasser plötzlich Geschmack bekommt. Galileo. ProSieben" Youtube, Mar. 12, 2018 (Mar. 12, 2018), pp. 1-1, Retrieved from the Internet: https://www.youtube.com/watch?v=SiCL5J7_TMA [retrieved on Feb. 21, 2020].

Hrfernsehen. "Serie: Hessen innovativ—Joyce" Youtube, Dec. 5, 2017 (Dec. 5, 2017), pp. 1-1, Retrieved from the Internet: https://www.youtube.com/watch?v=1AfLGzcoRN8 [retrieved on Feb. 21, 2020].

* cited by examiner

A-A

B-B

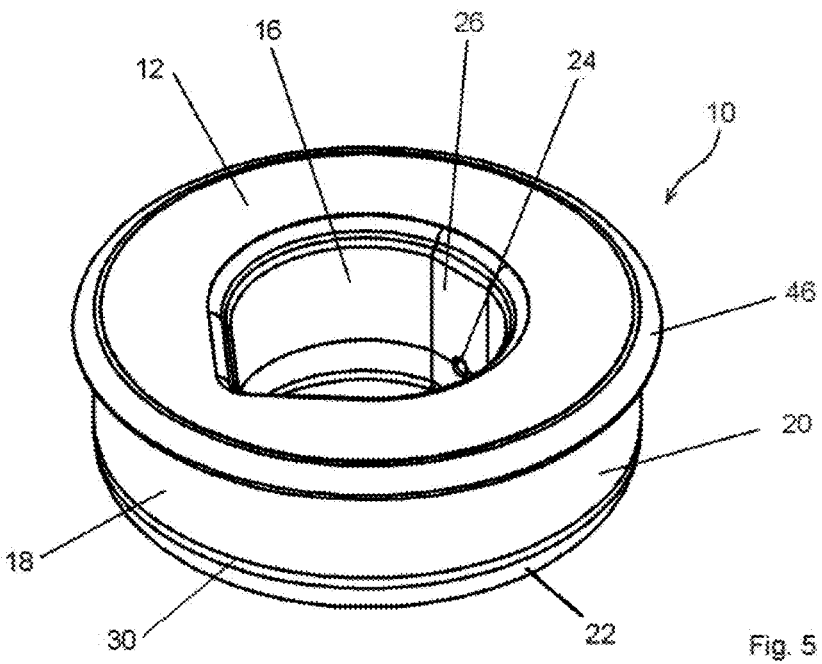
Fig. 5
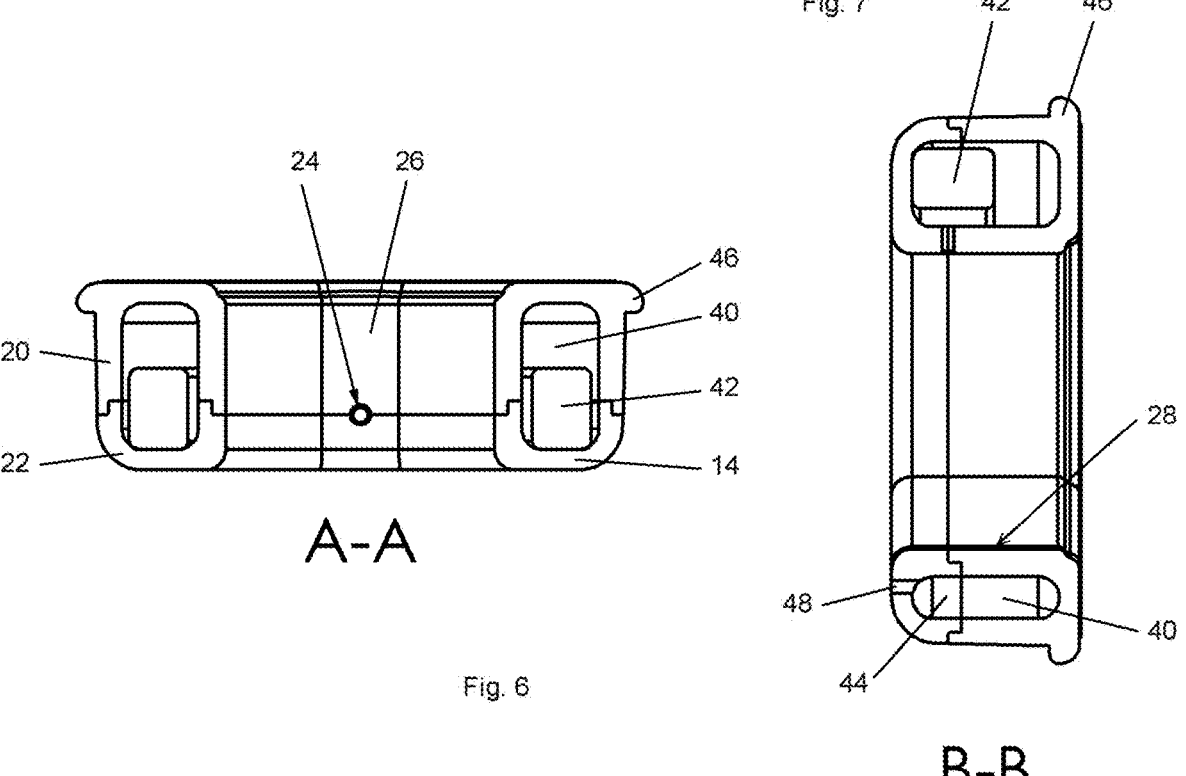
A-A
Fig. 6
Fig. 7
B-B

A-A

AROMA CONTAINER

RELATED APPLICATIONS

This application is a national stage filing under 35 U.S.C. 371 of International Patent Application No. PCT/EP2020/063793, filed May 18, 2020. The entire contents of this application is incorporated herein by reference in its entirety.

FIELD OF THE INVENTION

The invention relates to an aroma container and to drinking device having an aroma container of this kind.

PRIOR ART

There is an increasing demand for consuming drinking liquids which on the one hand have a pleasant flavour, but on the other hand avoid health risks which can be caused by consumption of aroma substances or stabilisers dissolved in the drinking liquid. Furthermore, the consumption of an increased number of calories should be avoided.

Therefore, water which is provided with a very slight fruit aroma has become popular in recent years. However, undesired additives, such as stabilising substances and a certain amount of sugar, are also contained in this aromatised water. Many users reject such drinks simply on account of this number of calories.

Since the olfactory sensation makes up a substantial part of the gustatory perception when consuming food and drinks, previous drinking systems attempt to influence the smell perceived upon drinking. For this purpose, aroma elements are proposed which can be fastened to a drinking container close to the drinking opening, in order that the aroma element is located in the direct vicinity of the user's nose, which user breathes through the nose during drinking, and thus ingests the scent.

A drinking device for retronasal ingestion of an aroma substance, comprising an aroma container through which air can flow and which supplies aromatised air to a transport channel for drinking liquid, is known from WO 2019/016096 A1. In this way, the aroma substance is ingested retronasally. During drinking, the aroma substance, together with the drinking liquid, enters the user's mouth, and subsequently rises retronasally via the pharynx to the olfactory mucosa, where it is sensed by the receptors located there, and perceived by the user. In this case, use is made of the fact that there is a close relationship between the sense of smell and the sense of taste. The user therefore acquires the impression that they are tasting the aroma, although they are actually only smelling it retronasally.

SUMMARY OF THE INVENTION

The object of the invention is that of proposing an aroma container for adding an aroma substance to an air flow flowing through the aroma container, which container allows for improved enrichment of the air, which has flowed through, with aroma substance.

This object is achieved by an aroma container having the features of claim 1 and by a drinking device having the features of claim 18. Preferred embodiments result from the remaining claims.

The aroma container according to the invention for adding an aroma substance to an air flow flowing through the aroma container comprises an upper wall, a lower wall and at least one side wall, which surround an aroma chamber, at least one air inlet opening into the aroma chamber, and at least one air outlet opening out of the aroma chamber. A carrier substance for the aroma substance is located in the aroma chamber. Furthermore, a head space between the carrier substance and the side of the upper wall facing the aroma chamber is preferably provided. According to the invention, the carrier substance furthermore comprises a nonwoven material, wherein the air permeability L of the nonwoven material at a differential pressure of 100 Pa is L≥200 $l/(m^2 \cdot s)$, and preferably between 220 $l/(m^2 \cdot s)$ and 280 $l/(m^2 \cdot s)$.

A carrier substance for the aroma substance is thus located in the aroma chamber, as well as, preferably, a head space between the carrier substance and the wall that closes the aroma chamber at the top. Providing a head space improves the mixing of the aromatised air flow. In this case, the air flow flowing through the aroma chamber flows through the carrier substance which is provided with the aroma substance. In the process, different partial flows form within the carrier substance, which comprises a nonwoven material, which partial flows can be aromatised to different extends, in particular if the aroma container has already been in use for a long time and there is no longer so much aroma substance in the carrier substance. During flow through the head space, which constitutes a cavity within the aroma chamber that is not filled with carrier substance, a homogenisation of the partial air flows, possibly aromatised to different extents, occurs. Providing a head space thus ensures that the user of a drinking device, who ingests the aromatised air flow in addition to drinking liquid, experiences a taste sensation that is as uniform as possible.

A further advantage of the head space is that of homogenising the aromatisation of the air flow with different aroma substances. Numerous aroma substances do not consist of one single chemical compound, but rather comprise a plurality of chemical compounds, the mass transfer behaviour of which is different from the carrier substance in the air flow. Individual partial air flows emerging from the carrier material can therefore have a different chemical composition of the aromatisation. Mixing the partial air flows in the head space generates an air flow which is provided as homogeneously as possible with aroma substance having the desired composition of the chemical compounds.

A further important aspect is that the air permeability of the nonwoven material at a differential pressure of 100 Pa is more than 200 $l/(m^2 \cdot s)$. Such an air permeability of the nonwoven material ensures that a good through-flow of the air flow flowing through the aroma container is ensured, but at the same time not too high a pressure drop occurs, which would impede the release of the aromatised air into the transport channel for drinking liquid of an associated drinking device.

Thus, the interplay of a carrier substance comprising a nonwoven material, which does not fill the entire aroma chamber but rather leaves a head space, is important, as well as the suitable selection of a high air permeability of the nonwoven material, which should be below 200 $l/(m^2 \cdot s)$.

The air permeability L of the nonwoven material at a differential pressure of 100 Pa is preferably no more than 500 $l/(m^2 \cdot s)$. If the air permeability is too high, there is a risk of preferred flow paths forming within the nonwoven material, through which flow paths the air flow flowing through the aroma container can flow at very low resistance, such that the air flow now has only a very slight tendency to flow through other regions of the nonwoven material and to take up the aroma substances present there. This would result in the air flow emerging from the aroma container exhibiting a reducing level of aromatisation, long before the aroma substance is actually exhausted.

The carrier substance in the aroma chamber does not have to have the same extension as the geometry of the aroma chamber. Thus, in addition to the head space provided in the vertical direction, between the carrier substance and the upper wall, there may also be one or more zones in the lateral direction, in the aroma container, in which the carrier substance is not contained, and in which increased homogenisation of the air flow flowing through the aroma container can occur.

If different aromas are used in a drinking device, the most suitable geometry with respect to the size of the head space, but also the lateral extension of the carrier substance in the aroma chamber, may differ among the individual aroma substances. Different aroma substances exhibit a different chemical structure, which influences their behaviour with respect to the mass transfer in the air flow.

If the carrier substance does not cover the entire lower wall of the aroma chamber, this may also have the advantage that, in the case of complex geometries of the cross-sectional area of the aroma chamber, the insertion of the carrier substance during production is facilitated.

The carrier substance preferably lies on the side of the lower wall facing the aroma chamber.

According to a preferred embodiment of the invention, the side wall of the aroma container comprises a protrusion, at least in portions, which preferably extends outwards, substantially perpendicularly to the outer side wall.

A protrusion of this kind facilitates the manual handling by a user who, in addition to suitable labelling, can identify on the basis of the protrusion the orientation in which the aroma container has to be coupled to an associated drinking device. Furthermore, as will be explained later, a protrusion extending outwards from the side wall can be used such that, in interaction with a correspondingly shaped drinking device, it automatically moves the aroma container into an operating position and, vice versa, also brings it into a position in which the aroma container can also be stored for a long period of time, because undesired emission from the aroma container is prevented.

The nonwoven material preferably has a specific flow resistance of less than 500 Pa·s/m and preferably less than 400 Pa·s/m, and most preferably of approximately 380 Pa·s/m. In this case, in accordance with the conventional definition, the ratio of the pressure difference before and after a material layer, to the speed of the air flowing through, is referred to as the specific flow resistance.

It is furthermore preferred for the nonwoven material to have an area density of less than 1500 g/m$^2$ and preferably of approximately 1000 g/m$^2$, and for the nonwoven material to have a density of less than 300 kg/m$^3$ and preferably a density of approximately 200 kg/m$^3$.

In this case, the area density, the maximum density, but also the preferred specific flow resistance, have been found to be particularly suitable parameters in order to allow a good through-flow of the carrier substance in the aroma chamber, but also a good enrichment of the air with aroma, and an improved aroma development during use of the aroma container in an associated drinking device.

Furthermore, 100% polyester is preferred as the nonwoven material since this is an inert material which does not enter into any undesired interaction with the aroma substances.

It has furthermore been found to be advantageous to arrange the carrier substance in the aroma chamber at a thickness of from 2 mm to 10 mm, and preferably of approximately 5 mm.

According to a preferred embodiment of the invention, the thickness of the carrier substance is at least 50% of the height between the upper wall of the aroma container and the lower wall of the aroma container, and preferably at least 80% of the height between the upper wall of the aroma container and the lower wall of the aroma container. If the upper wall and the lower wall of the aroma container do not extend in parallel with one another, the geometrically averaged thickness of the carrier substance and the geometrically averaged height of the aroma chamber in the region of the carrier substance are to be applied.

If the thickness of the carrier substance is less than 50% of the clear height within the aroma chamber, a sufficient flow through the nonwoven material no longer takes place. Therefore, in order to ensure a good flow through the nonwoven material, the thickness of the carrier substance is particularly preferably at least 80% of the height between the upper wall of the aroma container and the lower wall of the aroma container.

According to a further preferred embodiment, the carrier substance consists of more than one part, as is for example the case for granulates. Likewise, the carrier material can be divided at least once, substantially longitudinally or transversely, both with respect to the fibre direction of the material and with respect to the geometry of the aroma chamber. The allows for easier filling of the aroma chamber with the carrier material.

According to a particularly preferred embodiment of the carrier material, this is mixed with an aroma substance before being inserted into the aroma chamber, or is mixed with an aroma substance during or after being inserted into the aroma chamber. Likewise, the present invention can also be filled by the user themselves, or be designed so as to be refillable.

The height between the upper wall and the lower wall defines the height of the inner volume of the aroma chamber. The head space above the carrier substance should consequently be no more than half the height of the aroma container between the upper wall and lower wall, in the region of the carrier substance.

According to a preferred embodiment of the invention, the at least one air inlet opening has a diameter of at least 0.2 mm or a different geometry having an equivalent minimum opening cross-section.

A smaller opening cross-section of the air inlet opening than 0.2 mm is associated with too high a pressure drop, and therefore impedes the flow through the aroma container. Furthermore, a further reduction of the opening cross-section of the air inlet opening likewise does not have any advantages with respect to the flow regime prevailing in this region, which flow regime is in any case already in the turbulent region under typical operating conditions.

The porosity of the nonwoven material is preferably between 70% and 93%, and preferably between 70% and 80%.

A high porosity of the nonwoven material is important not only with respect to a good through-flow ability and a low specific flow resistance, but rather makes it possible for the carrier substance to be able to take up a large amount of aroma substance, such that an aroma container having small dimensions has a long service life until the supply of aroma substance is exhausted.

According to a preferred embodiment of the invention, the Reynolds number Re in the air inlet region of the aroma container is greater than 2000, wherein the Reynolds number is defined as $Re=(w \cdot d)/v$, with the kinematic viscosity of air $v$ [m²/s], the diameter $d$ [m] of the air inlet opening, and the flow speed $w$ [m/s] upon inflow into the aroma container at a time-averaged volume flow between 250 ml/min and 600 ml/min.

A Reynolds number of greater than approximately 2000 characterises a turbulent flow or at least a flow which is already in the transition region between a laminar and turbulent flow. A turbulent flow ensures good mixing, as a result of which the uptake of the aroma substance in the air flow flowing through the aroma container is improved. The volume flow per minute takes into account the sometimes significant fluctuations in the temporary volume flow when the aroma container according to the invention is coupled to a drinking device and the air outlet opening is in flow connection with a transport channel for drinking liquid. Since the drinking process is not a uniform, stationary process, but rather different pressures, but also different flow speeds, prevail in the transport channel for drinking liquid, within the context of the sucking and swallowing processes, there is a significant fluctuation of the temporary volume flows, and thus also flow speeds, at which the air passes through the air inlet opening. Experimentally, however, it has been possible to show that an average volume flow of between 250 ml/min and 600 ml/min flows through an aroma container according to the invention, when used as intended. In this case, the physiological drinking process was determined on a large number of different adult people. Since the volume flow is the product of the flow speed and the cross-sectional area, a suitable range for the opening cross-section of the air inlet opening can be determined, under the condition that the Reynolds number describing the flow state must be greater than 2000.

The air inlet opening preferably has a diameter of between 0.2 mm and 20 mm. Although a relatively large air inlet opening of 20 mm can ensure that there is no turbulent flow directly in the region of the air inlet opening, this can be compensated by the suitable selection of the geometry of the aroma chamber, for example in that the carrier substance rests directly on the air inlet opening, in the aroma chamber, and thus the air flow entering the aroma chamber flows through the carrier substance in a turbulent manner, within the nonwoven material.

According to a preferred embodiment of the invention, the aroma container has a substantially annular geometry comprising an outer side wall and an inner side wall.

A geometry of this kind has numerous advantages. Firstly, an aroma container of this kind can be fastened around the transport channel for drinking liquid, on the head part of a drinking device, without the weight of the aroma container being perceived as disruptive since an asymmetrical weight distribution on the drinking device does not occur. Furthermore, providing an annular geometry makes it possibly to purposely ensure, by the arrangement of the air inlet opening and the air outlet opening, that the air flow flowing through the aroma container travels the longest possible distance, and in the process flows through the carrier substance, contained in the aroma chamber, as completely as possible.

In the case of an aroma container having a substantially annular geometry, the inner side wall preferably surrounds a space, the cross-sectional area of which is of a geometry that deviates from a circular shape.

This design has numerous advantages, as will be described with reference to a plurality of examples. Firstly, the friction between the inner side wall and a head part of the drinking device, on which the aroma container is placed, can be reduced in a purposeful manner. Furthermore, a non-circular shape can be used to move the aroma container between different operating positions, in interaction with a suitably designed drinking device. Finally, a non-circular shape can also be used to facilitate correct placing of the aroma container on a drinking device, for a user.

In this connection, it is particularly advantageous to design the aroma container such that the geometry of the inner side wall defines just one single position of the aroma container with respect to the rotation thereof in cooperation with a correspondingly formed mouthpiece of a drinking device, wherein the space surrounded by the inner side wall preferably has a substantially drop-shaped cross-sectional area.

In other words, the geometry of the inner side wall of the aroma container is selected such that the space surrounded by the inner side wall has a cross-sectional area which allows a clear positioning of the aroma container. A hexagonal geometry of the inner side wall could not achieve this for example. Although the space surrounded by the inner side wall would have a geometry of the cross-sectional area that deviates from a circular shape, the aroma container could be placed in six different rotational positions on a correspondingly shaped mouthpiece filling the inner space.

It has been found to be particularly advantageous if, in the case of a substantially annular geometry of the aroma container, the cross-sectional area of which, however, deviates from a circular shape, for the ratio between a maximum extension ($L_{max}$) of the cross-sectional area of the space surrounded by the inner side wall, and the minimum extension ($L_{min}$) of the cross-sectional area of the space surrounded by the inner side wall, the following applies:

$$1.05 \le L_{max}/L_{min} \le 1.15;$$

and preferably $$L_{max}/L_{min} \text{ is approximately } 1.1$$

In this case, a geometry of the substantially annular aroma container that deviates from a circular geometry has been found to be advantageous not only with respect to possible clear positioning options, but rather also has the effect that the air flow flowing through the aroma container is better mixed by cross section changes and changes of the curvature of the aroma chamber, because all the changes in the flow pattern support the emergence of turbulences. If the ratio between the minimum extension and the maximum extension were to become too large, then in contrast this would again have negative consequences with respect to the travel distance for the air flow to flow through, with respect to the volume of the aroma chamber. In this case, the optimum is achieved in the case of a clean circular ring shape. The range between values of 1.05 and 1.1 for $L_{max}/L_{min}$ thus constitutes the best possible compromise between the longest possible travel distance for the air flow flowing through the aroma container on the one hand, and the assistance of the emergence of turbulences and/or the maintenance of existing turbulences on the other hand.

The aroma container preferably furthermore comprises slide ribs in the region of the inner side wall. Providing slide ribs reduces the friction when sliding the substantially annular aroma container onto a drinking device, in that the contact surface between the aroma container and the mouthpiece of the drinking device, extending in the space surrounded by the inner side wall, is reduced.

In the same way, however, it is also possible, instead of providing slide ribs, to provide grooves, which are provided in the inner side wall. This measure also reduces the potential contact surface between the aroma container and a possible shaping of the drinking device, and, associated therewith, the friction in the case of a relative movement between the two components.

If the grooves in the inner side surface of the aroma container extend sufficiently deeply inwards in the direction of the aroma chamber, this results in elevations being located on the side of the inner side wall facing the aroma chamber, which elevations extend into the aroma chamber and also assist the mixing of the air flow flowing through the aroma container, by means of the repeated separation of the flow of the air flow along the inner side wall.

Equally, it is also possible to reduce the friction in that the inner side wall of the aroma container in regions does not correspond to the outside shaping of the head part of the drinking device, and therefore contact between the aroma container and a drinking device over the entire surface does not occur.

Preferably, the air inlet opening is located in the region of the lower wall of the aroma container, and the air outlet opening is arranged in a side wall of the aroma container, preferably in an inner side wall in the case of a substantially annular geometry of the aroma container having an outer side wall and an inner side wall.

Providing the air inlet opening in the region of the lower wall of the aroma container is advantageous if the aroma container is intended to be fitted onto the head part of a drinking device and to come into sealing contact, there, with the head part of the drinking device. Furthermore, by providing the air inlet opening in the region of the lower wall of the aroma container, and depending on the arrangement of the carrier substance in the aroma container, a flow through the flow container can be generated, in the case of which the air flow has to flow through the carrier substance, during the flow through the aroma container, and does not flow directly into the head space provided in the aroma container.

Providing the air outlet opening in a side wall of the aroma container provides the possibility of generating a defined and long travel distance for the air flow flowing through the aroma container. For example, the air outlet opening can be located in a region in which the carrier substance rests, in the aroma chamber, on the air outlet opening. In this way, the air flow flowing through the aroma container has to flow through the carrier substance before emerging from the aroma container, and from there can emerge through the air outlet opening.

In the case of a substantially annular geometry of the aroma container having an outer side wall and an inner side wall, the air outlet opening is preferably located in the inner side wall of the aroma container, such that the aromatised air emerging from the aroma container can enter a transport channel for drinking liquid, which extends through the space surrounded by the inner side wall of the aroma container.

According to a preferred embodiment of the invention, the aroma container comprises a lower shell and an upper shell that is connected to the lower shell, wherein the air outlet opening is arranged in the connection region between the lower shell and upper shell.

This design has the advantage of being technically easy to implement within the context of production using an injection-moulding method. No slider is required for producing the air outlet opening.

A peripheral groove, which serves as a shadow gap and can fulfil a plurality of functions, is preferably located in the contact region between the lower shell and upper shell. Firstly, a shadow gap of this kind can show the user the position of an aroma container that is displaceable relative to the head part of a drinking device. Furthermore, the lower shell and upper shell can be interconnected by means of ultrasonic welding, without the risk of a material accumulation in the region of the weld seam extending outwards beyond the outer surface of the outer side wall.

According to a second aspect of the invention, this relates to a drinking device comprising an aroma container according to the invention and a head part which can be connected to the aroma container such that at least a portion of the aroma container is movable from an activated position into a non-activated position, wherein in the activated position the air outlet opening is in flow connection with a transport channel for drinking liquid in the drinking device, and in the non-activated position no flow connection exists between the air outlet opening and the transport channel for drinking liquid, and the air inlet opening is substantially sealed.

In this case it is possible, upon movement from an activated position into a non-activated position, for the aroma container to be moved completely, e.g. by a translational movement or by a rotational movement. It is likewise possible for just at least a part of the aroma container to be movable from an activated position into a non-activated position. Thus, for example, two parts of the aroma container, which are movable against one another, may be moved relative to one another, in that said parts are rotated relative to one another. It is likewise also possible to activate two parts of the aroma container by pulling apart or pushing together, wherein pulling apart the two parts makes it possible for the air outlet opening and/or the air inlet opening in the respective parts of the aroma container to be brought into a position in which they are flush with one another. In the simplest case, in the event of an annular aroma container, two housing parts may be rotatable against one another, and air outlet openings, which are provided in both housing parts, are in a position flush with one another, and the aroma container is in the activated position, only in a defined rotation position.

The drinking device is furthermore characterised in that, in the activated position, the air outlet opening of the aroma container is in flow connection with a transport channel for drinking liquid. According thereto, the aromatised air flow is not output into the ambient air, in order to act orthonasally in a user, but rather is fed into the transport channel for drinking liquid, such that the aromatised air is perceived retronasally by the user, and the sensory impression of a taste perception of the drinking liquid results.

The drinking device preferably comprises a removable cover which can be fitted to the head part of the drinking device, wherein the removable cover comprises at least one force-exerting element, by means of which the aroma container can be moved from a non-activated position into the activated position when the cover is removed.

The movement of the aroma container between the non-activated position and the activated position extends the service life of the aroma container since this does not emit unintentionally when it is not in operation. The movement of the aroma container between the non-activated position and the activated position can be performed by the user themselves, but there is always the risk of the user forgetting this. Therefore, the solution of providing the drinking device with a removable cover is advantageous. Said cover must be removed when it is intended to drink from the drinking device. If the drinking device comprises a force-exerting element, by means of which the aroma container can be moved automatically from the non-activated position into the activated position when the cover is removed, the drinking device is automatically in a state ready for use, having the aroma container in the activated position, following removal of the cover.

Equally, it is also possible to use the placement of the cover after the drinking process in order to bring the aroma container into the non-activated position.

According to a preferred embodiment of the invention, the at least one force-exerting element comprises a stop surface on the cover, by means of which the aroma container can be rotated from the non-activated position into the activated position in the case of a rotation of the cover when the cover is unscrewed. In other words, the rotational movement of the cover during unscrewing is used to rotate the aroma container from the non-activated position into the activated position. This operating principle can be used in the same way in order to rotate the aroma container from the activated position into the non-activated position, likewise with the aid of a contact surface on the cover of the aroma container, when the cover is screwed on.

According to an alternative embodiment of the invention, the side wall of the aroma container comprises a protrusion, at least in portions, which extends outwards. The at least one force-exerting element comprises an engagement element on the cover, preferably a hook-shaped element, which is arranged and designed so as to encompass the protrusion in a form-fitting manner during removal of the cover, and to move the aroma container from the non-activated position into the activated position.

For this purpose, a single, peripheral hook-shaped element can be provided, or a plurality of hook-shaped elements can be provided, on the cover, which element(s) snap in on the underside of the protrusion, on the side wall of the aroma container, when the cover is screwed onto the drinking device, and, upon removal of the cover, either by pulling off or unscrewing, draw the aroma container along therewith and bring it from the activated position into the non-activated position. In this case, at the end of the screwing-on process, in the activated position the aroma container can strike against a stop element, such that in the last portion of rotating on the cover the hook-shaped elements deform elastically and release the protrusion at the side wall of the aroma container again, such that the cover can be removed.

According to an alternative embodiment of the invention, the force-exerting element comprises a resilient preload element which is arranged between the aroma container and the head part of the drinking device and preloads the aroma container into the activated position when the cover is removed.

In this case, the resilient preload element can be a part which is formed integrally with the head part of the drinking device, or which is provided as a separate element. In the case of this solution, too, when the cover is removed the aroma container is moved, without further assistance by the user, from the non-activated position into the activated position.

BRIEF DESCRIPTION OF THE DRAWINGS

The invention will be explained in greater detail in the following, with reference to some embodiments. In the drawings:

FIG. 5 is an overall view of a second embodiment of an aroma container according to the invention;

FIG. 6 is a sectional view of the aroma container according to FIG. 5, analogously to the cutting plane A-A shown on the basis of the first embodiment in FIG. 2;

FIG. 7 is a sectional view of the aroma container according to FIG. 5, analogously to the cutting plane B-B shown on the basis of the first embodiment in FIG. 2;

FIG. 13a and

FIG. 13b are a three-dimensional view and a plan view of an aroma container according to a further embodiment of the invention in the activated position;

FIG. 14a and

FIG. 14b are a three-dimensional view and a plan view of the aroma container according to FIG. 13a in the non-activated position;

MODES OF IMPLEMENTING OF THE INVENTION

Figure 1:
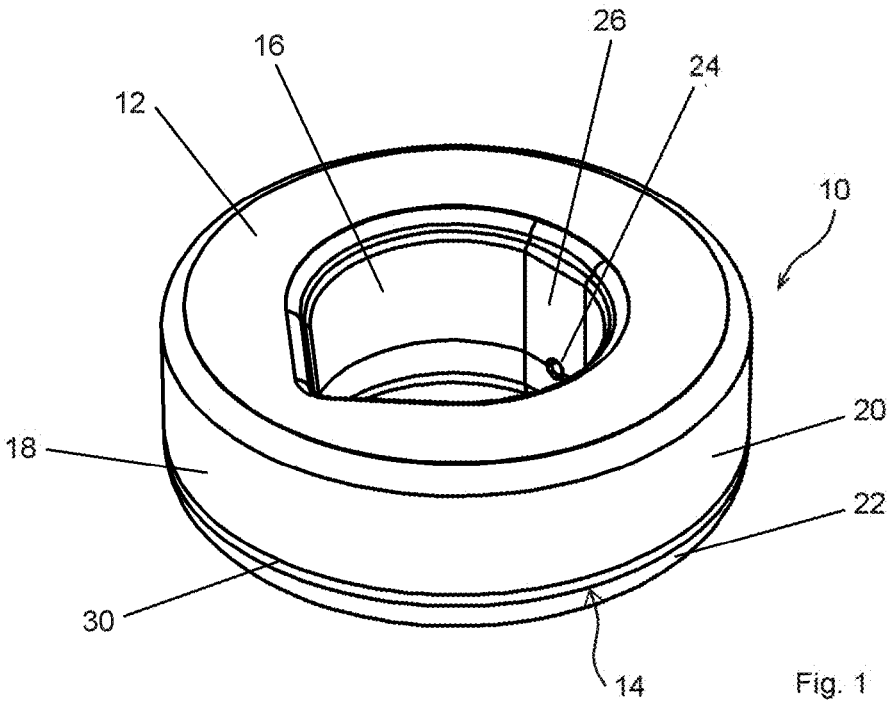
FIG. 1 is an overall view of an aroma container according to a first embodiment of the invention.

The invention will be explained in the following, purely by way of example, with reference to the embodiments shown in the drawings. In this case, terms such as upper, lower and lateral/side are used as though the aroma container, for example according to FIG. 1, were located having its lower wall lying on a horizontal, flat surface.

An aroma container 10 according to a first embodiment is shown in FIG. 1 to 4. In this case, the aroma container 10 comprises an upper wall 12, a lower wall 14, an inner side wall 16, and an outer side wall 18. As shown in particular in the sectional views according to FIGS. 3 and 4, the upper wall 12, lower wall 14, inner side wall 16 and outer side wall 18 surround an aroma chamber 40.

The upper wall 12 is preferably flat, at least in regions, in order that a label can be affixed to the outside of the upper wall 12.

The aroma container 10 according to FIG. 1 is substantially annular, comprising a circular ring-shaped outer side wall 18, and an inner side wall 16 which deviates from a circular shape. In other words, the space surrounded by the inner side wall 16 has a cross-sectional area which is not circular.

Figure 2:
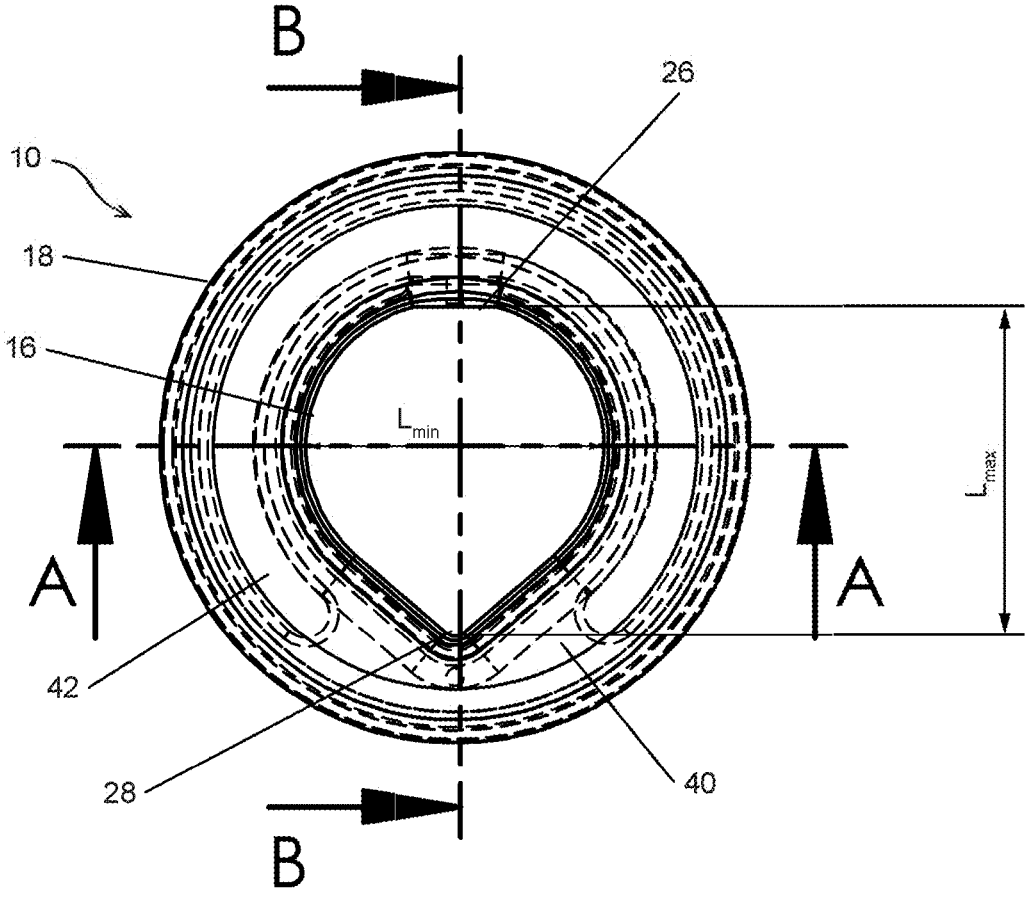
FIG. 2 is a plan view of the aroma container according to FIG. 1.

In the specific example, as is most clearly visible in the view according to FIG. 2, the inner side wall 16 is provided with a flat portion 26 and is otherwise approximately drop-shaped, having an end 28 substantially tapering to a point. As can be seen from FIG. 2, the illustrated geometry of the inner side wall 16 allows for clear positioning of the aroma container on a drinking device (not shown). In this case, the aroma container 10 can be placed on a correspondingly shaped element of the drinking device, the outer contour of which follows the geometry of the inner side wall to such an extent that the aroma container can be placed on the drinking device only in one single angular position, i.e. with respect to a rotation in the drawing plane of FIG. 2.

In this case, the geometry of the inner side wall 16 is selected such that the deviation of the inner contour from a circular ring shape is only slight. In this case, the ratio between the greatest clear dimension $L_{max}$ in the cross-sectional area of the space surrounded by the inner side wall 16, with respect to the smallest dimension $L_{min}$, ranges between 1.05 and 1.15, and is preferably approximately 1.1.

The flat portion 26 makes it possible to seal the air outlet opening 24 when the aroma container is pushed onto a correspondingly shaped geometry of the drinking device. Providing a flat sub-surface 26 in the region of the air outlet opening 24 is more suitable for this than a rounded surface.

The air outlet opening 24 is provided in the seam region between an upper shell 20 and a lower shell 22. This has the advantage that the aroma container can be easily manufactured since no separate slider has to be provided in the case of manufacture by injection moulding, but rather the upper shell 20 and lower shell 22 together form the air outlet opening 24.

A shadow gap 30, which fulfils various tasks, is provided in the region between the upper shell 20 and lower shell 22. Providing a shadow gap between the upper shell 20 and lower shell 22 can prevent material, escaping during welding of the upper shell to the lower shell, from optically impairing the appearance of the aroma container. Furthermore, providing the shadow gap makes it possible to achieve rounded edges. A further advantage of providing the shadow gap 30 is that the user can be visually given feedback of the operating position in which the aroma container is located, in that said container can be displaced in a vertical direction, relative to the drinking device, and in the process, in an arrangement of the aroma container displaced vertically downwards the shadow gap is no longer visible for the user.

The contour of the inner side wall 16 is vertical, i.e. the space surrounded by the inner side wall has a constant cross-sectional dimension over the height of the aroma container. This allows for vertical displacement of the aroma container relative to an element of a drinking device, which extends through the space surrounded by the inner side wall and rests on the inner side wall. Providing an inner side wall having a vertical extension is advantageous in all embodiments of the invention.

Figure 4:
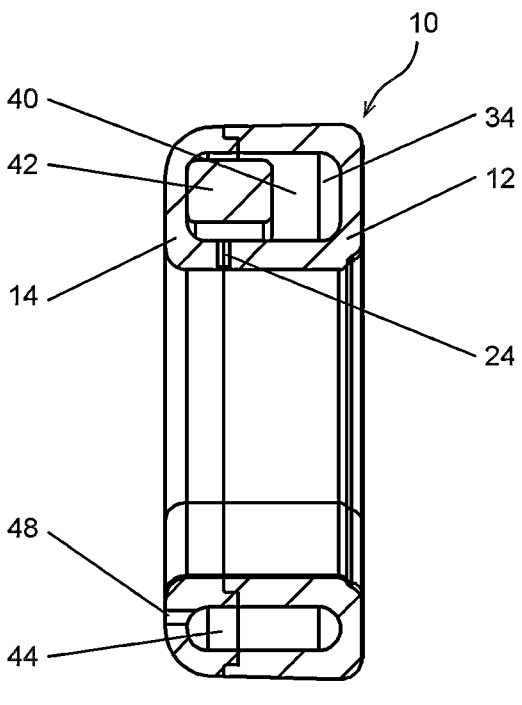
FIG. 4 is a sectional view of the aroma container along the cutting line B-B in FIG. 2.

The air inlet opening 48 is shown in FIG. 4 and is located in the lower wall 14 of the aroma container. In this case, the air inlet opening 48 is preferably located in the lower wall 14, in the region of the end 28 that tapers to a point, and thus diametrically opposed to the air outlet opening 24. Consequently, the air flow flowing through the aroma container has to travel as wide a travel distance as possible, and can thus be enriched with aroma substance in a particularly effective manner.

Figure 3:
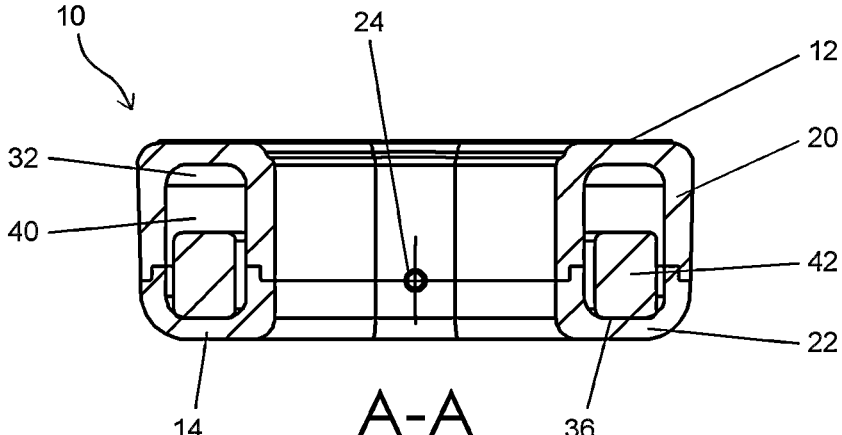
FIG. 3 is a sectional view of the aroma container along the cutting line A-A in FIG. 2.

As shown in the sectional views according to FIGS. 3 and 4, the aroma chamber 40 is located in the interior of the aroma container 10. Furthermore, a carrier substance 42 is inserted in the aroma chamber 40, which carrier substance carries the aroma substance. The carrier substance is, as shown in FIG. 2, U-shaped, i.e. not completely peripheral, with the result that the insertion of the carrier substance by machine, into the lower shell 22 of the aroma container, prior to placement of the upper shell 20, can be facilitated during the production process. The U-shaped geometry of the carrier substance furthermore allows for a better aroma development since, in the embodiment according to FIG. 1 to 4, in the region of the end 28 tapering to a point the air first enters into an air-filled space 44 of the aroma chamber 40, and can subsequently enter the carrier substance 42 uniformly over the entire height thereof, and flow through the carrier substance.

As is also shown in FIGS. 3 and 4, a head space is located above the carrier substance, in which head space the aroma chamber 40 is not filled with carrier substance 42. Providing a head space also has the function of allowing improved enrichment of the air, as well as a homogenisation of the air with aroma substance.

As shown in FIGS. 3 and 4, in this case the carrier substance 42 is inserted into the aroma chamber 40 such that the carrier substance rests on the side 36 of the lower wall 14 facing the aroma chamber. The head space 32 is consequently provided between the carrier substance 42 and the side 34 of the upper wall 12 facing the aroma chamber. In this case, the head space 32 is of a height which is less than 50% of the height of the aroma chamber 42, i.e. less than 50% of the spacing between the side 34 of the upper wall 12 facing the aroma chamber and the side 36 of the lower wall 14 facing the aroma chamber. It is preferred, however, for the carrier substance to occupy at least 80% of the height of the aroma chamber.

In all the embodiments shown, the carrier substance is a nonwoven material which, at a differential pressure of 100 Pa, has an air permeability L of $L \geq 200$ $l/(m^2 \cdot s)$, and preferably between 220 $l/(m^2 \cdot s)$ and 280 $l/(m^2 \cdot s)$. The nonwoven preferably consists of 100% polyester. In this case, the porosity of the nonwoven material is between 70% and 93%, preferably between 70% and 80%.

In the embodiment according to FIG. 1 to 4, the diameter of the air inlet opening in the lower wall is 1.2 mm.

Since the upper shell 20 and lower shell 22 are interconnected by means of ultrasonic welding methods, the upper shell and lower shell are connected in a sealed manner other than in the region of the air outlet opening, such that a possible penetration of air into the aroma container, or an undesired escape of aroma substance, for example during storage, from the aroma container can be prevented.

Figure 8:
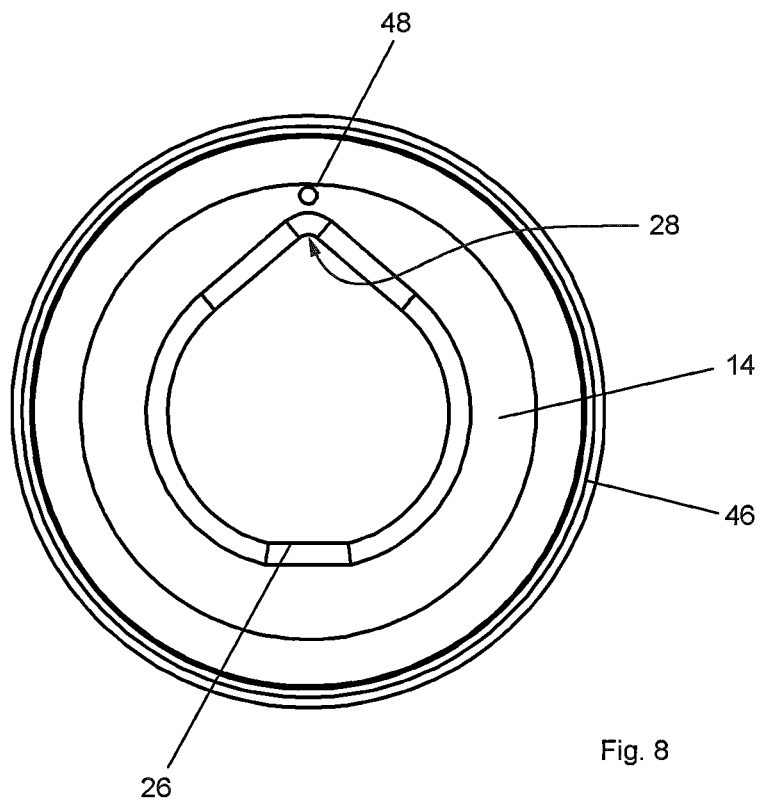
FIG. 8 is a view from below of the aroma container according to FIG. 5.

The embodiment of the aroma container 10 shown in FIG. 5 to 8 differs from the aroma container according to FIG. 1 to 4 merely in that a protruding region 46 is provided on the outer side wall 18 of the aroma container. In the embodiment of FIGS. 5 and 8, the protruding region 46 is designed as a peripheral edge, but can equally also comprise individual, separate sub-portions. In the same way, in the embodiment according to FIGS. 5 and 8 the peripheral edge is arranged in a plane with the upper wall 12, which likewise merely constitutes an example. It is equally possible to provide the protruding portion(s) at any desired position of the side wall. Finally, it should also be clear that the overall geometry of the aroma container shown in FIG. 5 to 8 is likewise to be understood merely by way of example. The aroma container does not have to be ring-shaped. All that is important is that the side wall should comprise a protrusion, at least in portions. In this case, it is preferable for the protrusion to extend outwards, substantially perpendicularly to the outer side wall.

The protruding region 46 shown in the embodiment according to FIGS. 5 to 8 makes it possible for the aroma container to be more easily gripped by a user. In a specific embodiment, which will be explained below, in interaction with a drinking device the protruding region 46 can also be used to move the aroma container, in a comfortable manner, between a non-activated position and an activated position, or to separate it from the drinking device.

The protruding region 46 only has to have a slight radial extension in order to facilitate gripping of the aroma container for a user. For example, in general an extension of from 0.6 mm to 1.5 mm towards the outside is sufficient to offer the user additional purchase when gripping the aroma container and removing it upwards. With respect to the vertical height of the peripheral edge, too, it is sufficient for the peripheral edge to be of a thickness, i.e. vertical extension, of between 2.0 mm and 2.5 mm. In the case of conventional plastics materials, from which the aroma container is preferably produced, providing a thickness of the peripheral edge in this range makes it possible to achieve sufficient stability.

Figure 9:
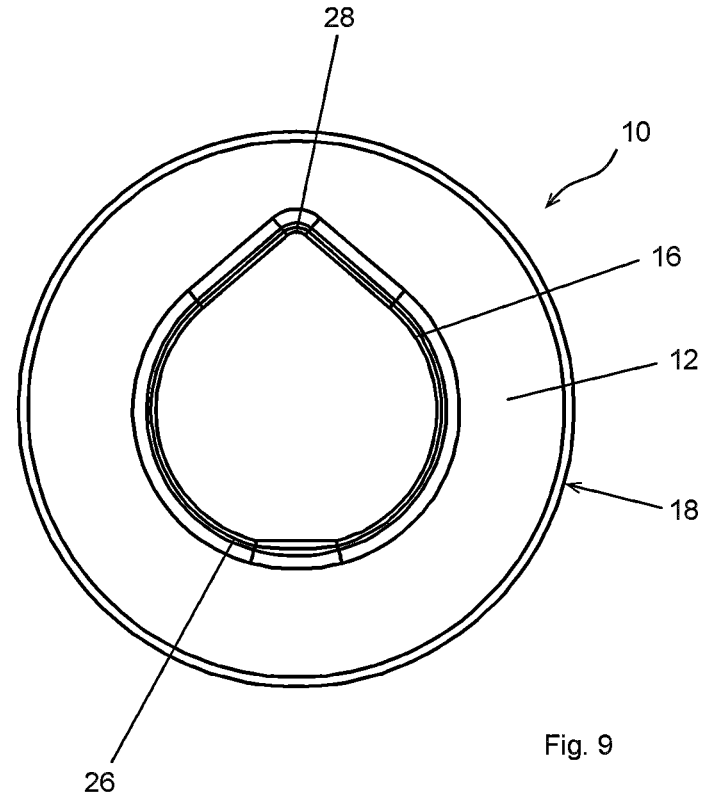
FIG. 9.
Figure 10:
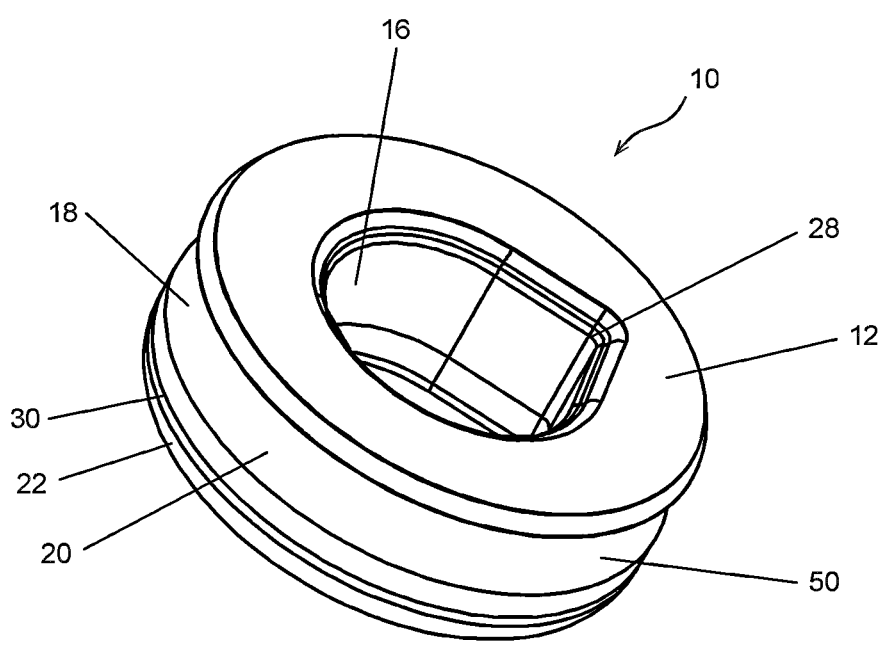
FIG. 10 are a plan view and a three-dimensional view of an aroma container according to a further embodiment of the invention.

FIGS. 9 and 10 are a plan view and a three-dimensional view of a further alternative embodiment of an aroma container according to the invention. The aroma container according to FIGS. 9 and 10 is constructed in a manner similar to the aroma container according to the preceding embodiments, but has a recessed handle 50 in the region of the side wall 18. In this case, the aroma container according to FIGS. 9 and 10 can also be provided with an edge which is provided in portions or is peripheral, as in the embodiment according to FIG. 5 to 8. The recessed handle 50 makes it possible for the user to be able to better grip the aroma container when pushing the aroma container onto the head part of an associated drinking device, as a result of which the actuation of the aroma container is simplified.

In addition to a protruding portion such as the protruding region 46, shown by way of example, and a recessed handle 50, other geometries are also conceivable, which allow for easier gripping of the aroma container. For example, this can also be achieved by providing a suitable surface structure of the side wall, such as a textured surface, or the use of coatings, for example comprising elastomers.

In numerous embodiments, in each case reference is made to a substantially circular ring-shaped geometry of the aroma container having a circular ring shape on the outside on an approximate drop shape on the inside, in order to be able to better point out the specific differences between the individual embodiments. Nonetheless, it should be clear that the aroma container according to the invention is not restricted to a geometry of this kind. In the following, as an example for the different geometries reference is made to FIGS. 11 and 12, which show an aroma container 10 which is designed so as to be substantially U-shaped.

Figure 12:
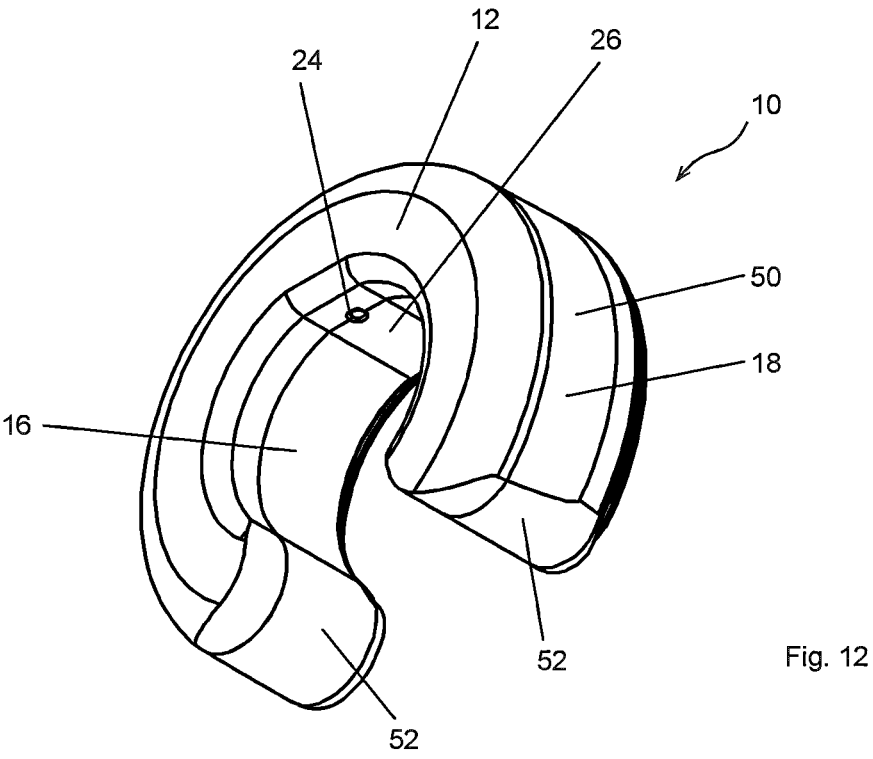
FIG. 12 are a plan view and a three-dimensional view of an aroma container according to a further embodiment of the invention.

The aroma container according to FIGS. 11 and 12 again comprises an upper wall 12, a lower wall 14, an inner side wall 16, and an outer side wall 18. The outer side wall 18 can, as in the embodiment of the aroma container according to FIGS. 9 and 10, be provided with a recessed handle 50 arranged concavely in the side wall 18. In the same way, the aroma container according to FIGS. 11 and 12 could also be provided with a 46 protruding region, as has been described with reference to the embodiment according to FIGS. 5 to 8. As shown in FIG. 12, the air outlet opening 24 is provided in the centre of the U-shaped geometry of the aroma container, in the region of a flat portion 26.

Figure 11:
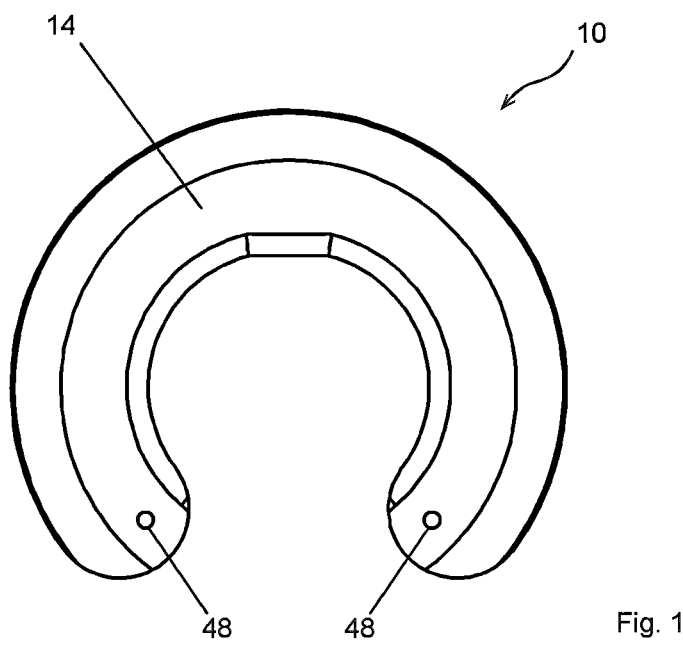
FIG. 11.

In a manner deviating from the preceding embodiments, the aroma container 10 according to FIGS. 11 and 12 is provided with two air inlet openings 48, which are each located in the region of the free end 52 of the U-shaped profile and ensure that the aroma substance located in the carrier substance of the aroma chamber is take up by the air flow, flowing through, from the region of both free ends 52.

The aroma container 10 shown in FIGS. 13a, 13b, 14a and 14b comprises a closure attachment 54 which is located in the region of the inner side wall 16, in the region of the air outlet opening 24. In the embodiment shown, the closure attachment 54 is rigidly connected to the upper wall 12, but the operating principle described in the following can equally also be implemented if the closure attachment is rigidly connected to the lower wall instead of to the upper wall. The closure attachment extends along the inner side wall 16, into the space surrounded by the inner side wall, and is arranged along the inner side wall, at a close spacing.

Figures 13A, 13B, 14A, 14B:
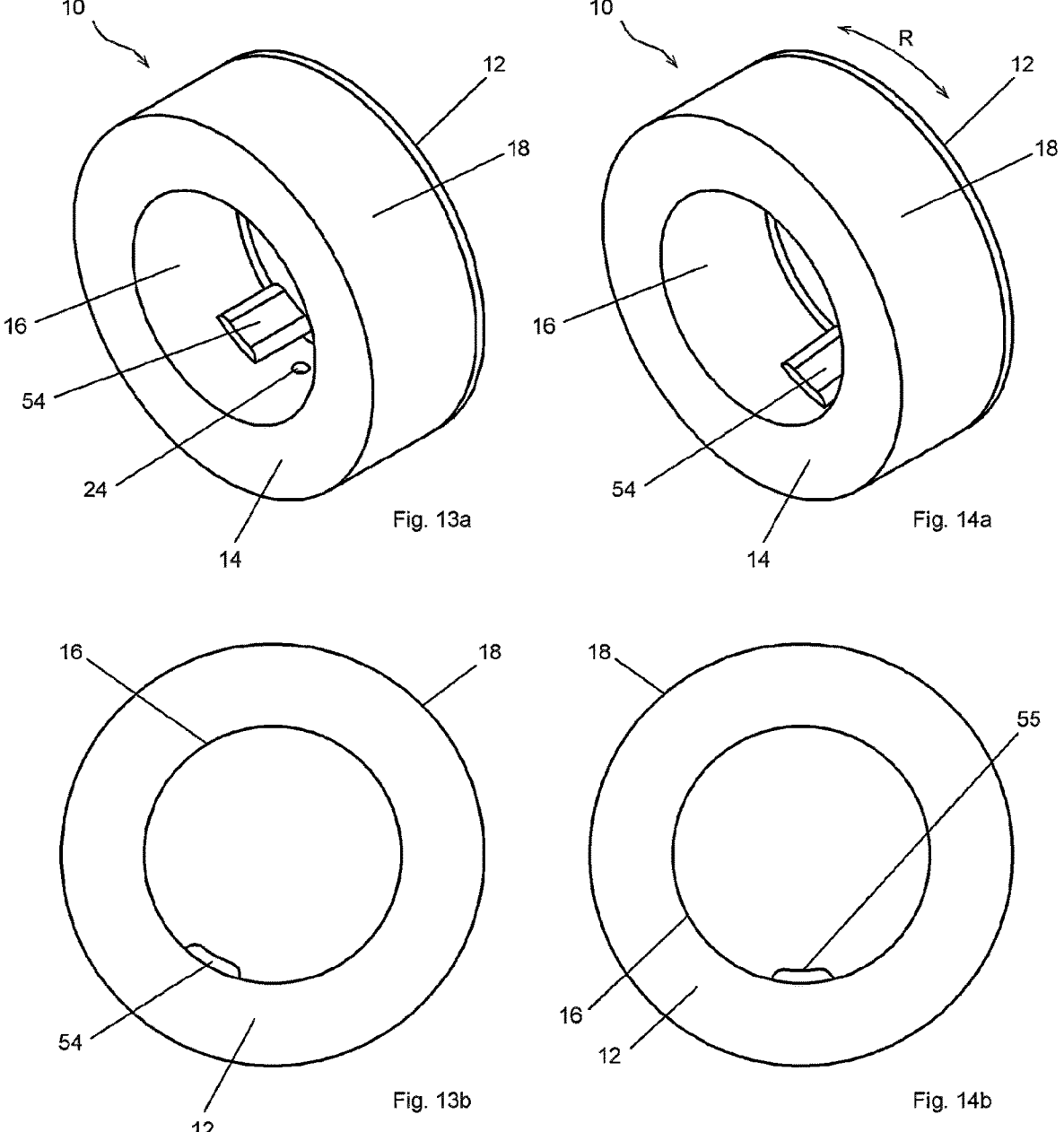

The closure attachment 54 serves to move the aroma container 10 between an activated position, shown in FIGS. 13a and 13b, and a non-activated position, shown in FIGS. 14a and 14b. In the activated position the air outlet opening 24 is free, while in the non-activated position the air outlet opening 24 is closed by the closure attachment 54.

For this purpose, the upper wall 12 is rotatable relative to the wall portion of the inner side wall 15 in which the air outlet opening 24 is located. The user can thus move the aroma container 10 between the activated position shown in FIG. 13a and the non-activated position shown in FIG. 14a, by rotating the upper wall 12 in the rotation direction R.

In this case, the rotation R can be brought about in that a user grips the aroma container at the upper wall 12 and rotates said upper wall relative to the lower wall 14. Alternatively, the user could also displace the closure attachment 54 using a finger. For this purpose, the closure attachment can, as in the embodiment shown, comprise a concavely shaped gripping surface 55 and improve the contact between a finger and the closure attachment 54 in another, suitable manner.

Figure 15:
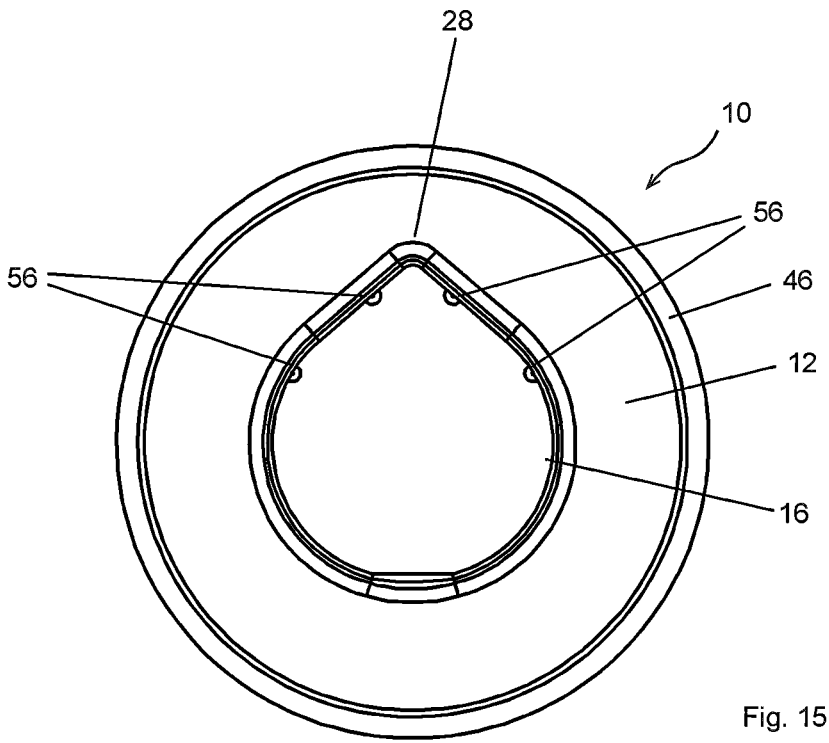
FIG. 15.
Figure 16:
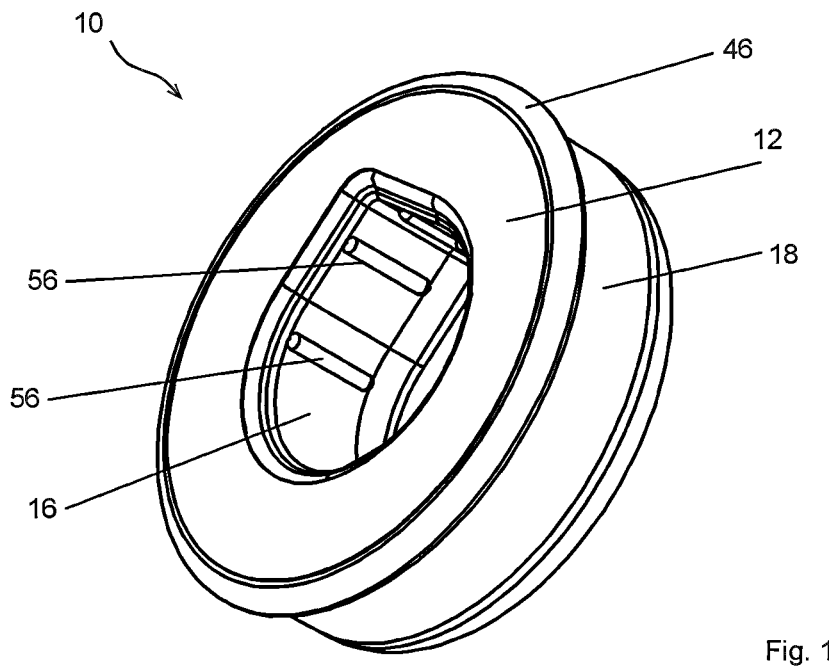
FIG. 16 are a plan view and a three-dimensional view of an aroma container according to a further alternative embodiment of the invention.

FIGS. 15 and 16 show an embodiment of the aroma container according to the invention, in which slide ribs 56 extend from the inner side wall 16 into the space surrounded by the inner side wall. In this case, the slide ribs extend in the vertical direction and have a rounded contour that faces away from the inner side wall 16, such that substantially only linear contact between the aroma container 10 and the head part of a drinking device can be established in the region of the slide ribs 56, which contact extends through the space surrounded by the inner side wall 16 of the aroma container.

The slide ribs 56, which extend in the vertical direction of the aroma container, additionally serve to guide the aroma container, and to allow for straight removal of the aroma container from a drinking device.

In the following embodiments, design variants are shown in which an aroma container is movable between an activated position and a non-activated position.

In the embodiment according to FIG. 17 to 20, the aroma container is moved between the activated and non-activated position in that the upper shell 20 and the lower shell 22 of the aroma container 10 are movable relative to one another. For this purpose, as can be seen from the sectional views in FIGS. 18 and 20, the upper shell 20 and the lower shell 22 are displaceable against one another, in the vertical direction.

Figures 17, 18, 19, 20:
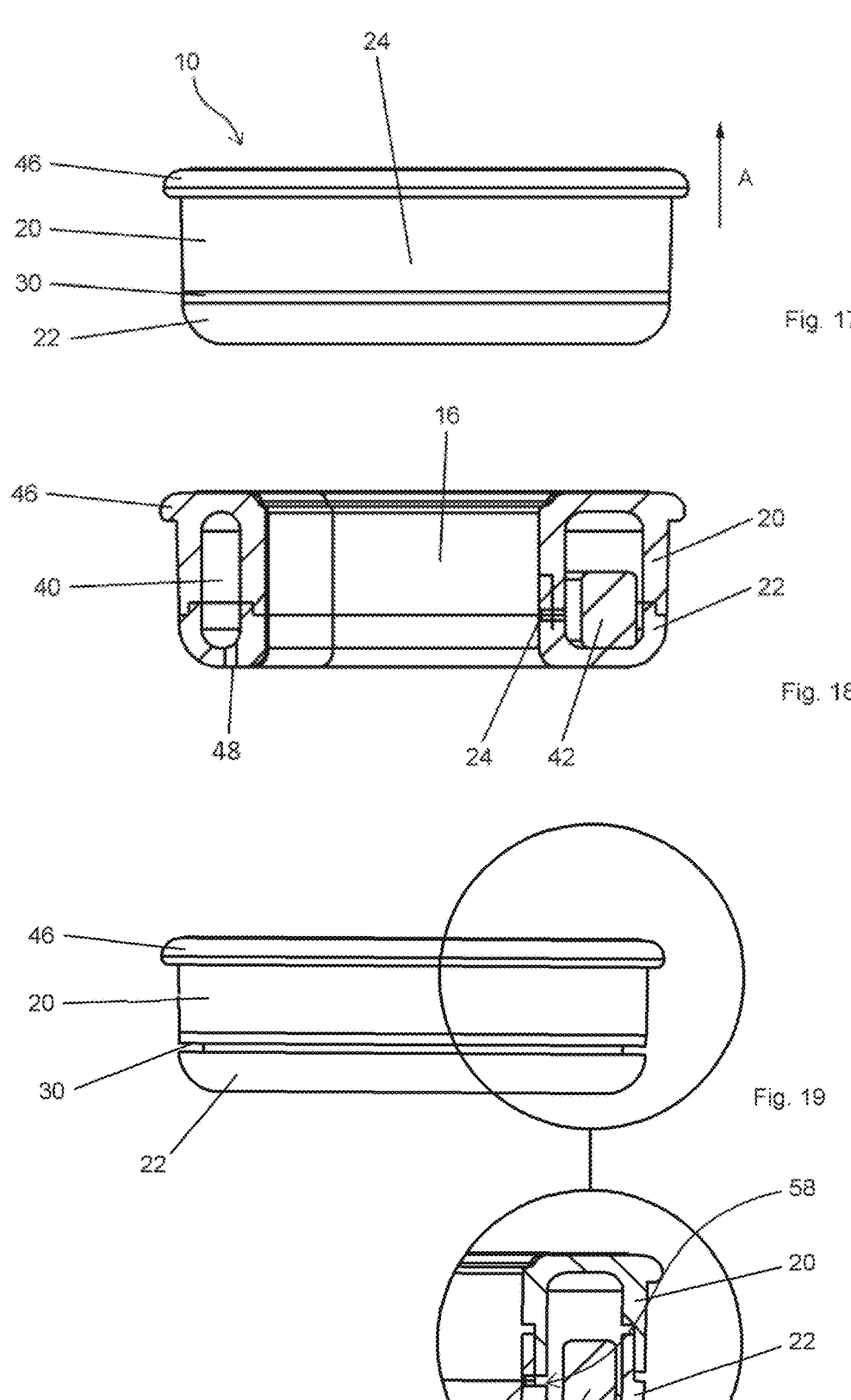
FIG. 17.
FIG. 18 show a further embodiment of an aroma container according to the invention in a first, non-activated position.
FIG. 19 shows the aroma container according to FIG. 17 in an activated position.
FIG. 20 is a detailed cross-sectional view of the aroma container according to FIG. 19 in the activated position.

In this case, the aroma container can interact with a drinking device such that the head part of the drinking device moves through the space surrounded by the inner side wall 16. In this case, the lower wall 14, in which the air inlet opening 48 is located, can rest on the head part of the drinking device, in the non-activated state which is shown in FIG. 18, in such a way that the air inlet opening 48 is sealed. Furthermore, in the non-activated state the air outlet opening 24 is also closed. If the aroma container is now pulled vertically upwards, in that either a user or, as will be explained later, the cover of the drinking device, grips the protruding region 46 from below and pulls the aroma container upwards in the arrow direction A, the upper shell 20 and lower shell 22, which are guided displaceably against one another, are pulled apart, as a result of which the passage 58 in the region of the air outlet opening 24 is formed (see FIG. 20). In this way, in the case of the vertical movement of the aroma container in the arrow direction A, both the air inlet opening 48 and the air outlet opening 24 are opened, and the aroma container is thus brought into an activated position ready for operation.

Figures 21, 22:
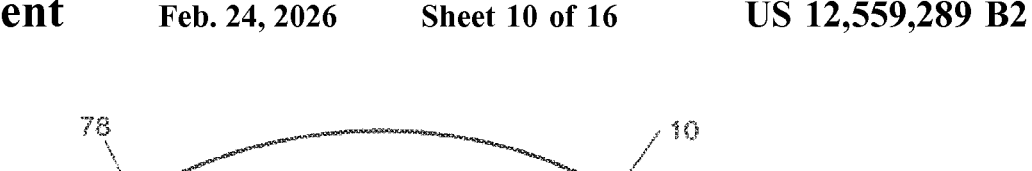
FIG. 21.
FIG. 22 shows an embodiment of the drinking device according to the invention comprising a cover for automatically actuating the aroma container.

The embodiment according to FIGS. 21 and 22 shows an alternative design of an aroma container 10 which, upon actuation of a cover 70 of the drinking device, is movable between the activated and the non-activated position. For this purpose, the cover 70 is either unscrewed from the drinking device or screwed thereon, in the rotation direction B.

In this case, the cover is designed such that it is movable freely and independently of the aroma container, but in the last portion of the complete screwing onto the drinking device comes into engagement with an upper edge region 74 of the aroma container, by means of an entrainment surface 72. In this case, when the cover is screwed onto the drinking device, in the clockwise direction, the aroma container is thus moved together therewith, such that the aroma container is in a non-activated state in which the air outlet opening is no longer flush with a corresponding inlet opening in the transport channel for drinking liquid, and therefore no aromatic air can be output from the aroma container. The rotation of the aroma container can equally also be performed manually by the user.

In the same way, when the cover is unscrewed from the drinking device according to FIG. 21, the entrainment surface 76 of the cover can come into engagement with the upper edge region 78 of the aroma container 10, and move the aroma container along therewith, according to the arrow direction B in FIG. 21, until the aroma container is in an activated position and the entrainment surface 76 of the cover, due to the movement upwards in the drawing plane of FIG. 21, is no longer in engagement with the upper edge region 78, such that the aroma container thus remains in its activated position during the further rotation of the cover.

Figure 23:
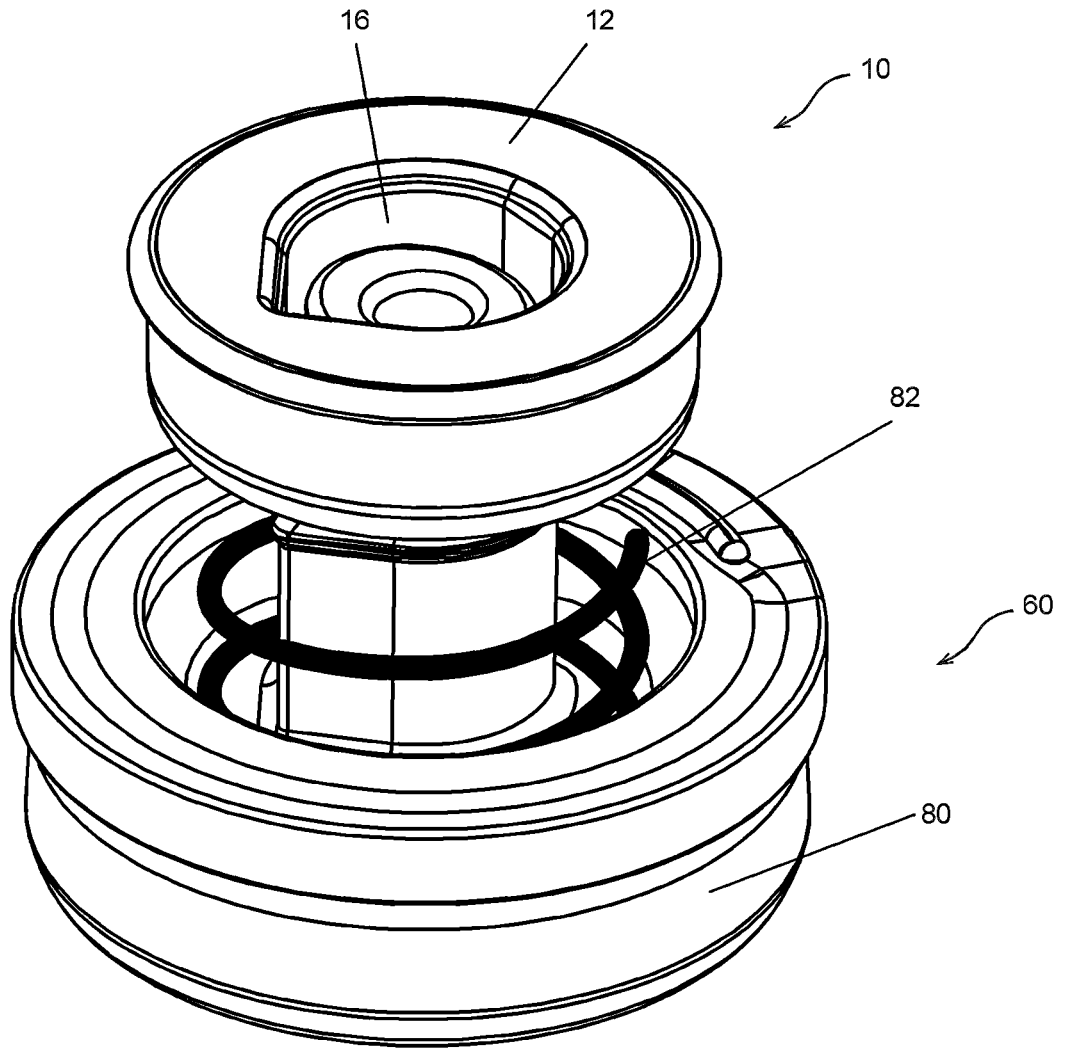
FIG. 23 shows an embodiment of the drinking device according to the invention comprising a first alternative possibility of a force-exerting element.

FIG. 23 shows an alternative possibility, by means of which the aroma container 10 can be automatically brought into an activated position, in interaction with a drinking device 60, when no vertical pressure acts on the aroma container 10 any longer, by means of opening a cover. For this purpose, a resilient element, in the present case a helical spring 82, is provided in the region of the head part 80 of the drinking device, which spring preloads the aroma container 10 vertically upwards. In the illustration according to FIG. 23, the aroma container is shown not in the activated position, but rather during placement of the aroma container on the head part 80 of the drinking device, in order that the helical spring 82 is visible. During operation, and in particular during the movement of the aroma container between a non-activated position and an activated position, it is sufficient for the helical spring 82 to move the aroma container upwards merely by a small travel distance, where the aroma container strikes a stop at the part of the head part 80 which extends through the space formed by the inner side wall 16. In this way, when the cover is unscrewed the resilient preload of the helical spring 82 moves the aroma container upwards, against a stop, by a defined travel distance, where said container is in the activated position. In the same way, upon opening the cover, pressure is exerted on the upper wall 12 of the aroma container 10, and this is displaced downwards, in the vertical direction, into the non-activated position.

Figure 24:
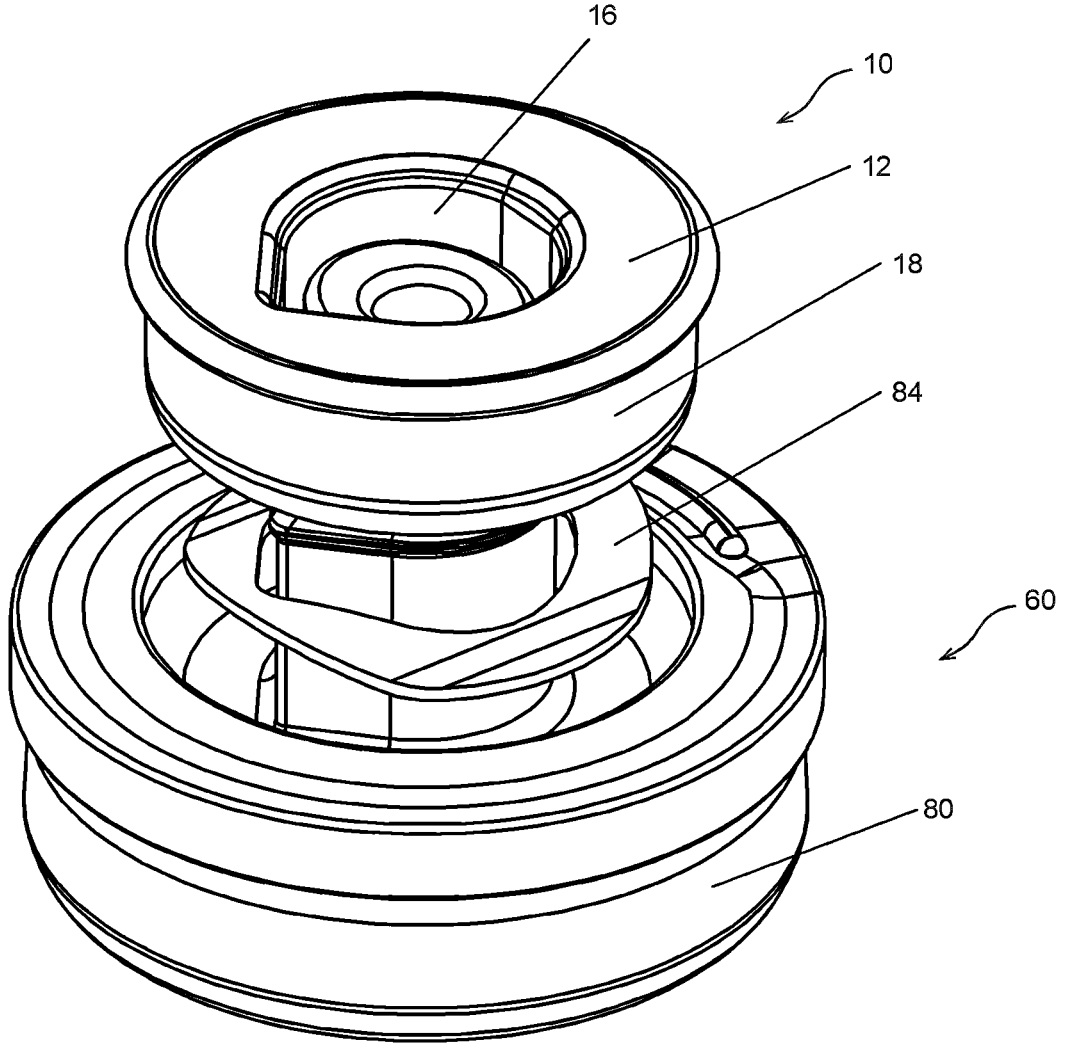
FIG. 24 shows an embodiment of the drinking device according to the invention comprising a second alternative possibility of a force-exerting element.
Figure 25:
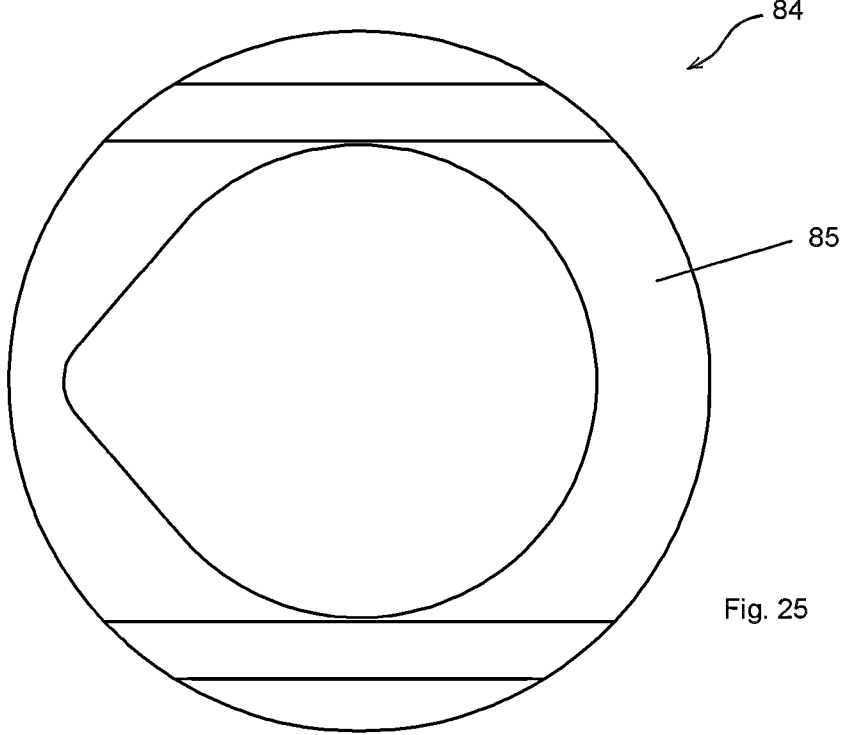
FIG. 25.
Figure 26:
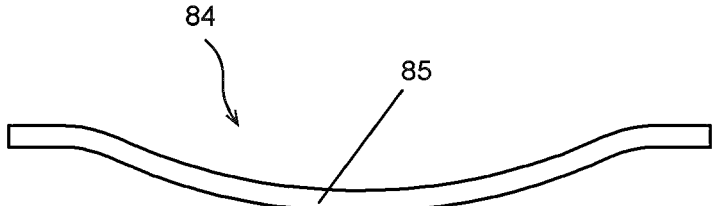
FIG. 26 shows a plan view and a side view of the force-exerting element according to FIG. 24.
Figure 27:
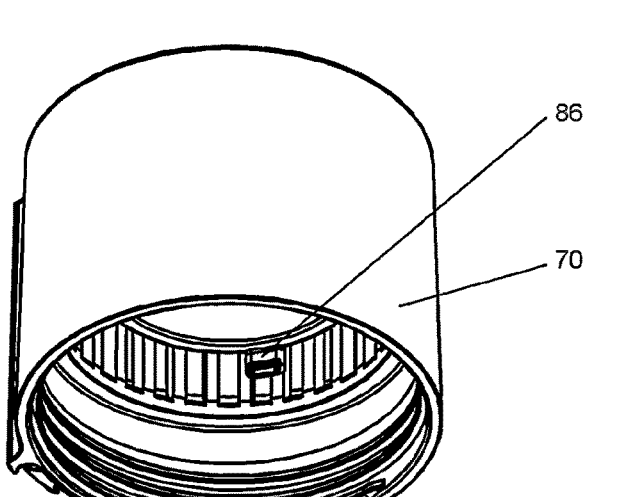
FIG. 27 shows a cover of a drinking device according to the invention for automatically actuating the aroma container.

The embodiment according to FIG. 24 to 26 differs from that according to FIG. 23 merely in that a spring ring 84 is provided instead of the helical spring 82. The spring has the advantage, compared with the helical spring 82 according to the embodiment according to FIG. 23, that it is easier to clean.

The spring ring can be provided as a separate component, which is inserted into a depression in the head part 80 of the drinking device 60 and displaces the aroma container 10 vertically upwards, from the non-activated position, into the activated position, as soon as the cover (not shown in FIG. 24) is removed from the drinking device and no longer exerts any pressure on the upper wall 12 of the aroma container. In this case, a shape of the spring ring 24 given by way of example is shown in FIGS. 25 and 26, from which it is evident that the spring ring is merely an annular plate having a curved, elastically deformable central part 85, which can be easily cleaned by a user.

Figure 28:
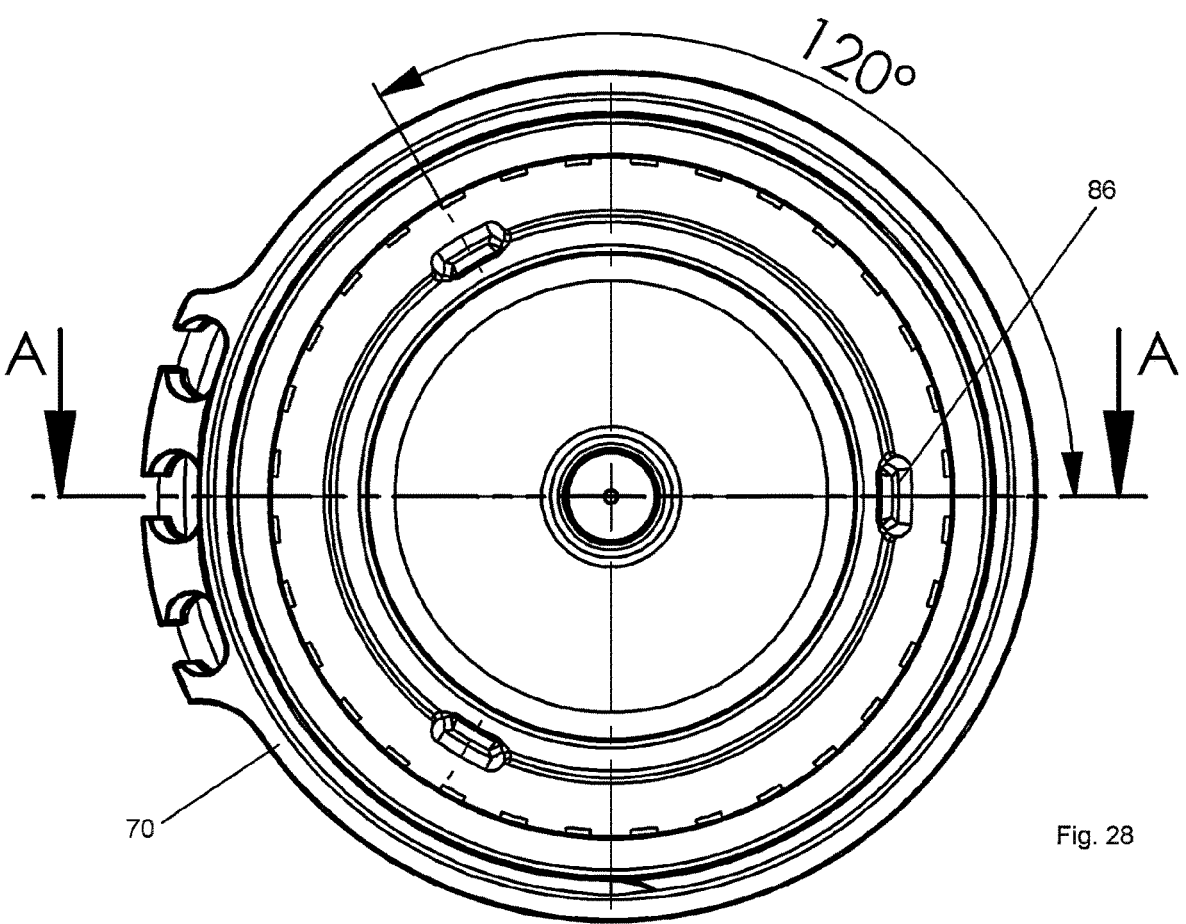
FIG. 28 is a view from below of the cover according to FIG. 247.
Figure 29:
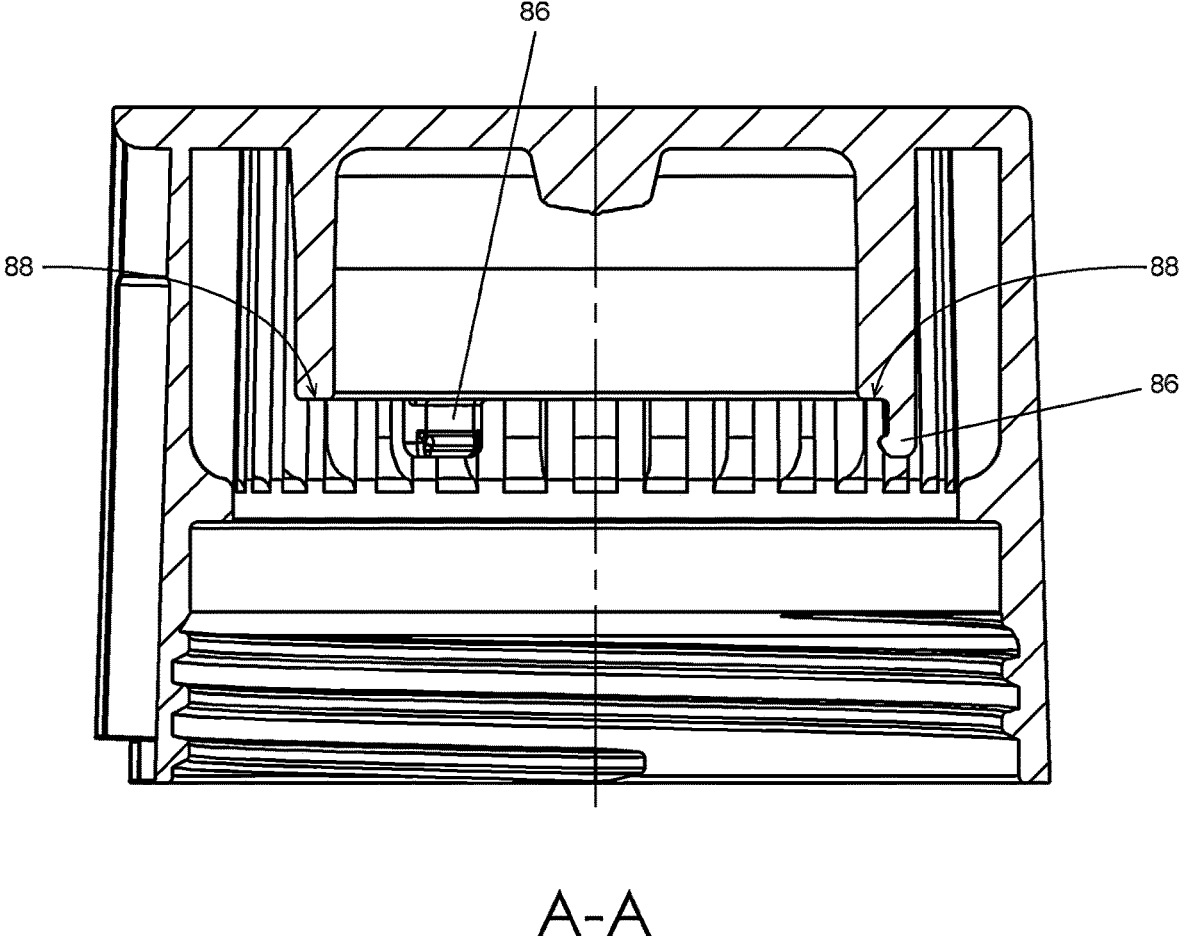
FIG. 29 is a sectional view in the direction A-A in FIG. 28.
Figure 30:
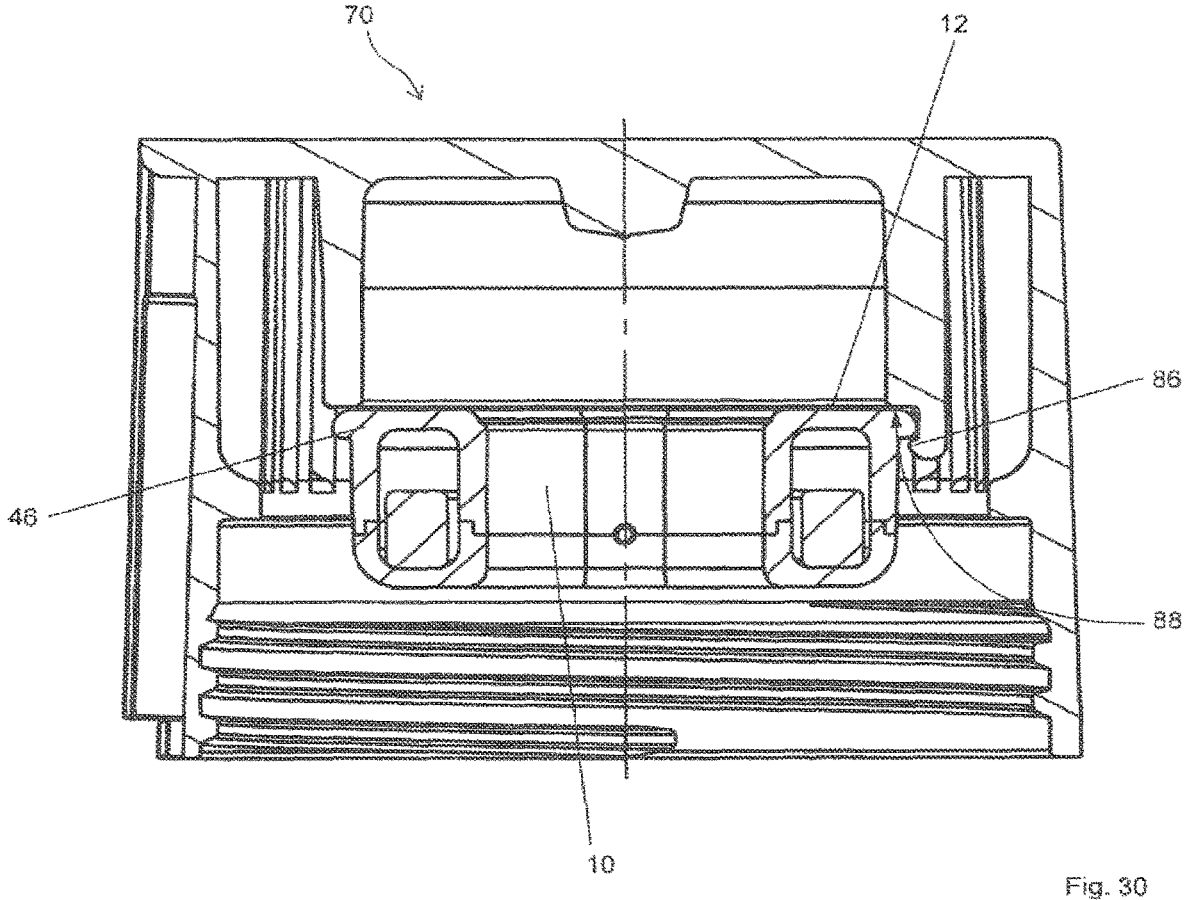
FIG. 30 is a sectional view explaining the interaction of the cover according to FIG. 27 with an aroma container according to FIG. 5.

FIG. 27 to 30 show the cover 70 and the interaction thereof with an aroma container 10 according to the embodiment of FIG. 5 to 8, which allows for an automatic movement of the aroma container between the non-activated position and the activated position. In this case, the cover 70 of the drinking device is provided with at least one engagement hook, in the embodiment according to FIG. 27 to 30 with three engagement hooks 86, which, as is most clearly evident from the view of FIG. 28, are uniformly distributed over the periphery of an inner surface of the cover 70. In this case, the geometry of an engagement hook 86 in cross section can be seen from the sectional view in FIG. 29. In this case, the engagement hooks extend downwards from the stop surface 88 in the cover. In this case, the stop surface 88 has the function of positioning the upper wall 12 of the aroma container 10. The aroma container is provided with a peripheral edge 46, in order, as shown in FIG. 30, to be able to grip the engagement hook 86 in a form-fitting manner. The aroma container 10 is exactly positioned on the head part of the drinking device, with respect to the angle, such that the aroma container does not rotate when the cover is rotated, but rather the engagement hooks 86 are moved around the peripheral edge 46 in the case of a rotation of the cover, and, upon unscrewing of the cover upwards, pull the aroma container 10 upwards therewith.

When the cover is unscrewed, the aroma container is pulled upwards until it strikes a stop. As soon as the aroma container has been pulled upwards as far as its activated position, i.e. its operating position, and strikes the stop on the mouthpiece of the drinking device (not shown), the engagement hooks deform in the event of a further vertical movement of the cover 70 upwards, and in the process come out of engagement with the peripheral edge 46 of the aroma container.

If, following use of the drinking device, during which the aroma container 10 is in the upwardly pulled, activated position, the cover is closed again, then the engagement hooks 86 snap over the peripheral edge 46 of the aroma container. The upper wall 12 of the cover 70 then rests against the stop surface 88 of the cover 70 such that, in the event of a further vertical movement of the cover downwards, for example during screwing of the cover onto a thread on the head part of the drinking device, the aroma container is pushed vertically downwards, until the aroma container is in the non-activated position in which the outlet opening is no longer in flow connection with a corresponding inlet opening into the transport channel for drinking liquid, and the air inlet opening 48 arranged on the underside of the aroma container is pressed against a sealing surface on the head part of the drinking device.

Thus, in this embodiment too, the user no longer has to move the aroma container back and forth between the non-activated and the activated position since this occurs automatically when the cover is unscrewed and screwed on. However, if the user does not wish to consume aromatised drinking liquid, it is of course possible to manually push the aroma container vertically downwards into the non-activated position before drinking.

In addition to the variants described above, by means of which the aroma container can be moved automatically between the activated and the non-activated position, further solutions, which are not described in detail here, are also conceivable. For example, the aroma container can be pulled upwards by means of a magnetic coupling of the aroma container to the cover. Instead of a screw connection, a bayonet connection between the cover and the drinking container can equally also be provided.

It is likewise possible to provide a hinged cover, either with or without a spring element, which, upon opening, either releases the aroma container, such that it can be displaced into the activated position by means of a spring element, or, by means of ramp-like oblique surfaces on the cover, automatically slightly rotates the aroma container upon opening and closing of the cover, in order to move said container between the activated position and the non-activated position.

Finally, it is also possible to design the aroma container such that it is movable automatically from a non-activated into an activated position, when negative pressure is applied. In this solution, the moving part of the aroma container is a non-return valve which opens automatically in the event of a negative pressure during use of the drinking device, and releases the air outlet opening of the aroma container.

What is common to all the solutions described above is that the aroma container is designed such that the Reynolds number Re in the air inlet region is greater than 2000, wherein the Reynolds number is defined as Re=(w·d)/v, with the kinematic viscosity of air v [m²/s], the diameter d [m] of the air inlet opening, and the flow speed w [m/s] upon inflow into the aroma container at a time-averaged volume flow between 250 ml/min and 600 ml/min. The geometry of the aroma chamber is preferably designed such that, in the case of this volume flow of air flowing into the aroma container, a turbulent air flow prevails in the entire aroma container, wherein the local Reynolds number, which characterises the local flow state at a particular point in the aroma container, instead of the diameter d of the air inlet opening, with the aid of the largest free flow cross section, in each case, is formed in the local region of the aroma container.

The embodiments described above describe individual advantageous designs of the aroma container according to the invention, which can be combined with one another as far as is expedient, and also combined with one another in further embodiments that are not described in detail.

LIST OF REFERENCE CHARACTERS

10 aroma container
12 upper wall
14 lower wall
16 inner side wall
18 outer side wall
20 upper shell
22 lower shell
24 air outlet opening
26 flat portion
28 end tapering to a point
30 shadow gap
32 head space
34 the side of the upper wall facing the aroma chamber
36 the side of the lower wall facing the aroma chamber
40 aroma chamber
42 carrier substance
44 air-filled space of the aroma chamber
46 peripheral edge
48 air inlet opening
50 recessed handle
52 free end of the aroma container
54 closure attachment
55 gripping surface
56 slide rib
58 passage
60 drinking device
70 cover
72 entrainment surface
74 upper edge region
76 entrainment surface
78 upper edge region
80 head part
82 helical spring
84 spring ring
85 curved central part
86 engagement hook
88 stop surface

The invention claimed is:

1. An aroma container configured for adding an aroma substance to an air flow flowing through the aroma container for retronasal perception, the aroma container comprising:
    an upper wall, a lower wall and at least one side wall, which surround an aroma chamber,
    at least one air inlet opening into the aroma chamber; and

19 at least one air outlet opening out of the aroma chamber; wherein a carrier substance for the aroma substance is present in the aroma chamber; and the carrier substance includes a nonwoven material; wherein the air permeability L of the nonwoven material at a differential pressure of 100 Pa is L≥200 l/(m²·s).

2. The aroma container according to claim 1, wherein a head space between the carrier substance and the side of the upper wall facing the aroma chamber is provided.

3. The aroma container according to claim 1, wherein the side wall includes a protruding region, at least in portions.

4. The aroma container according to claim 3, wherein the protruding region extends outwards, substantially perpendicularly to the side wall.

5. The aroma container according to claim 1, wherein the nonwoven material has a specific flow resistance of less than 500 Pa·s/m.

6. The aroma container according to claim 5, wherein the nonwoven material has a specific flow resistance of less than 400 Pa·s/m.

7. The aroma container according to claim 6, wherein the nonwoven material has a specific flow resistance of approximately 380 Pa·s/m.

8. The aroma container according to claim 1, wherein the nonwoven material has an area density of less than 1500 g/m²; and the nonwoven material has a density of less than 300 kg/m³.

9. The aroma container according to claim 8, wherein the nonwoven material has an area density of approximately 1000 g/m²; and a density of approximately 200 kg/m³.

10. The aroma container according to claim 1, wherein the thickness of the carrier substance is at least 50% of the height between the upper wall of the aroma container and the lower wall of the aroma container.

11. The aroma container according to claim 10, wherein the thickness of the carrier substance is at least 80% of the height between the upper wall of the aroma container and the lower wall of the aroma container.

12. The aroma container according to claim 1, wherein the at least one air inlet opening has a diameter of at least 0.2 mm or a different geometry having an equivalent minimum opening cross-section.

13. The aroma container according to claim 12, wherein the at least one air inlet opening has a diameter of no more than 20 mm.

14. The aroma container according to claim 1, wherein porosity of the nonwoven material is between 70% and 93.

15. The aroma container according to claim 14, wherein the porosity of the nonwoven material is between 70% and 80%.

16. The aroma container according to claim 1, wherein the Reynolds number Re in the air inlet region of the aroma container is greater than 2000;

wherein the Reynolds number is defined as Re=(w·d)/v, with the kinematic viscosity of air v [m²/s], the diameter d [m] of the air inlet opening, and the flow speed w [m/s] upon inflow into the aroma container at an averaged volume flow between 250 ml/min and 600 ml/min.

17. The aroma container according to claim 1, wherein the aroma container has a substantially annular geometry comprising an outer side wall and an inner side wall.

18. The aroma container according to claim 17, wherein the inner side wall surrounds a space, the cross-sectional area of which is of a geometry that deviates from a circular shape.

19. The aroma container according to claim 18, wherein the geometry of the inner side wall allows the aroma container to remain stationary in response to a rotational movement of a corresponding cover element.

20. The aroma container according to claim 19, wherein the space surrounded by the inner side wall has a substantially drop-shaped cross-sectional area.

21. The aroma container according to claim 18, wherein for the ratio between a maximum extension $L_{max}$ of the cross-sectional area of the space surrounded by the inner side wall, and the minimum extension $L_{min}$ of the cross-sectional area of the space surrounded by the inner side wall, the following applies: $1.05 \leq L_{max}/L_{min} \leq 1.15$.

22. The aroma container according to claim 21, wherein $L_{max}/L_{min}$ is approximately 1.1.

23. The aroma container according to claim 18, further comprising slide ribs in the region of the inner side wall.

24. The aroma container according to claim 1, wherein the air inlet opening is located in the region of the lower wall of the aroma container; and the air outlet opening is arranged in a side wall of the aroma container.

25. The aroma container according to claim 24, wherein the air outlet opening is arranged in an inner side wall in the case of a substantially annular geometry of the aroma container having an outer side wall and an inner side wall.

26. The aroma container according to claim 1, wherein the aroma container comprises a lower shell and an upper shell that is connected to the lower shell, wherein the air outlet opening is arranged in a connection region between the lower shell and upper shell.

27. The aroma container according to claim 1, wherein the air permeability L of the nonwoven material at a differential pressure of 100 Pa is between 220 l/(m²·s) and 280 l/(m²·s).

28. A drinking device, comprising an aroma container according to claim 1; and a head part, to which the aroma container is connectable such that at least a part of the aroma container is movable from an activated position into a non-activated position; wherein in the activated position, the air outlet opening is in flow connection with a transport channel for drinking liquid in the drinking device; and in the non-activated position, there is no flow connection between the air outlet opening and the transport channel for drinking liquid.

29. The drinking device according to claim 28, wherein the drinking device comprises a removable cover which is configured to be fitted to the head part of the drinking device; and the drinking device comprises at least one force-exerting element configured to move the aroma container from the non-activated position into the activated position when the cover is removed.

30. The drinking device according to claim 29, wherein the at least one force-exerting element includes an entrainment surface on the cover configured to rotate the aroma container from the non-activated position into the activated position in the case of a rotation of the cover when the cover is unscrewed.

31. The drinking device according to claim 29, wherein the side wall of the aroma container includes a protruding region, at least in portions, which extends outwards; and the at least one force-exerting element includes a hook-shaped element on the cover, which is arranged and designed so as to encompass the protrusion in a form-fitting manner during removal of the cover, and to move the aroma container from the non-activated position into the activated position.

32. The drinking device according to claim 29, wherein the force-exerting element includes a resilient preload element which is arranged between the aroma container and the head part of the drinking device, and preloads the aroma container into the activated position when the cover is removed.

33. The drinking device according to claim 28, wherein the air inlet opening is substantially sealed in the non-activated position.

* * * * *